United States Patent [19]

Ahr et al.

[11] Patent Number: 4,463,045

[45] Date of Patent: Jul. 31, 1984

[54] MACROSCOPICALLY EXPANDED THREE-DIMENSIONAL PLASTIC WEB EXHIBITING NON-GLOSSY VISIBLE SURFACE AND CLOTH-LIKE TACTILE IMPRESSION

[75] Inventors: Nicholas A. Ahr; Paul R. Louis; William I. Mullane, Jr.; William R. Ouellette, all of Cincinnati, Ohio

[73] Assignee: The Procter & Gamble Company, Cincinnati, Ohio

[21] Appl. No.: 349,098

[22] Filed: Feb. 16, 1982

Related U.S. Application Data

[63] Continuation-in-part of Ser. No. 239,875, Mar. 2, 1981, abandoned.

[51] Int. Cl.$^3$ ............................................. B32B 3/00
[52] U.S. Cl. ..................................... 428/131; 428/141; 428/913; 604/370
[58] Field of Search .............. 604/370, 371, 384, 385; 428/131, 134–137, 147, 156, 255, 913, 141, 143

[56] References Cited

U.S. PATENT DOCUMENTS

| | | | |
|---|---|---|---|
| Re. 23,910 | 12/1954 | Smith et al. | 264/555 |
| Re. 29,524 | 1/1978 | Spencer | 428/134 |
| 691,804 | 1/1902 | Parker | 428/48 |
| 2,166,366 | 7/1939 | Norris | 430/6 |
| 2,776,452 | 1/1957 | Chavannes | 264/555 |
| 2,809,392 | 10/1957 | Armstrong | 425/385 |
| 2,816,025 | 12/1957 | Dahlberg | 430/463 |
| 2,820,985 | 1/1958 | Cresswell | 425/463 |
| 2,857,657 | 10/1958 | Wheeler, Jr. | 29/156.8 H |
| 2,926,490 | 3/1960 | Eaton et al. | 60/267 |
| 3,054,148 | 9/1962 | Zimmerli | 264/504 |
| 3,123,446 | 3/1964 | Wheeler, Jr. | 428/593 |
| 3,137,746 | 6/1964 | Seymour et al. | 264/73 |
| 3,154,461 | 10/1964 | Johnson | 428/159 |
| 3,174,837 | 3/1965 | Mears | 428/596 |
| 3,252,844 | 5/1966 | Hechelhammer et al. | 156/2 |
| 3,390,447 | 7/1968 | Mears | 228/174 |
| 3,415,796 | 12/1968 | Souder et al. | 428/141 |
| 3,484,835 | 12/1969 | Trounstine et al. | 428/179 |
| 3,540,959 | 11/1970 | Connor | 156/203 |
| 3,560,601 | 2/1971 | Johnson et al. | 264/93 |
| 3,760,940 | 9/1973 | Bustin | 206/58 |
| 3,790,431 | 2/1974 | Tung | 428/255 |
| 3,814,101 | 6/1974 | Kozak | 604/370 |
| 3,843,478 | 10/1974 | Zuscik | 428/220 |
| 3,844,027 | 10/1974 | Hagen et al. | 228/209 |
| 3,911,187 | 10/1975 | Raley | 428/180 |
| 3,929,135 | 12/1975 | Thompson | 604/385 |
| 3,957,414 | 5/1976 | Bussey, Jr. et al. | 425/384 |
| 3,979,494 | 9/1976 | Ericson | 264/154 |
| 3,989,867 | 11/1976 | Sisson | 428/132 |
| 4,038,040 | 7/1977 | Nagl | 428/596 |
| 4,041,951 | 8/1977 | Sanford | 604/375 |
| 4,190,692 | 2/1980 | Larsen | 428/107 |
| 4,248,822 | 2/1981 | Schmidt | 264/154 |
| 4,254,182 | 3/1981 | Yamaguchi et al. | 428/372 |
| 4,259,286 | 3/1981 | Louis et al. | 264/555 |
| 4,321,924 | 3/1982 | Ahr | 604/385 |
| 4,327,730 | 5/1982 | Sorensen | 604/370 |
| 4,342,314 | 8/1982 | Radel et al. | 425/138 |
| 4,343,848 | 8/1982 | Leonard, Jr. | 428/156 |

FOREIGN PATENT DOCUMENTS

| | | |
|---|---|---|
| 18684 | 11/1980 | European Pat. Off. . |
| 2014508 | 8/1979 | United Kingdom . |
| 2014903 | 9/1979 | United Kingdom . |

OTHER PUBLICATIONS

Article entitled "S-P-2 Solprene Plastomer Blends in LPDE Film"–published by Phillips Petroleum Company, Stow, Ohio–No publication date.

Primary Examiner—William J. Van Balen
Attorney, Agent, or Firm—E. Kelly Linman; John V. Gorman; Richard C. Witte

[57] ABSTRACT

A macroscopically expanded three-dimensional plastic web exhibiting a non-glossy visible surface, and, if desired, a cloth-like or fiber-like tactile impression. The visible surface of a macroscopically expanded three-dimensional plastic web of the present invention is preferably provided with a regularly spaced, microscopic pattern of surface aberrations which is too fine to be discernible by the naked eye when the perpendicular distance between the viewer's eye and the plane of said web is about 12 inches or greater, but which pattern is effective in substantially eliminating specular reflection of incident light. Said webs may be produced by means of a one-sided forming process wherein said surface aberrations are transmitted through the thickness of said web during processing or by means of a two-sided forming process wherein said surface aberrations are imposed directly onto the visible surface of said web. Macroscopically expanded three-dimensional plastic webs of the present inveniton may be effectively employed as alternatives for cloth and fibrous structures which contact the wearer's skin, as well as for new and existing product applications where a non-plastic visual and tactile impression are desired.

9 Claims, 23 Drawing Figures

MACROSCOPICALLY EXPANDED THREE-DIMENSIONAL PLASTIC WEB EXHIBITING NON-GLOSSY VISIBLE SURFACE AND CLOTH-LIKE TACTILE IMPRESSION

CROSS-REFERENCE TO RELATED APPLICATION

This application is a continuation-in-part of co-pending application Ser. No. 239,875 filed Mar. 2, 1981, now abandoned in the name of the present applicants.

TECHNICAL FIELD

The present invention has relation to resilient plastic webs exhibiting many of the three-dimensional, cloth-like properties and characteristics previously obtainable only in fibrous webs.

The present invention has further relation to resilient plastic webs which exhibit a combination of desirable, but previously incompatible attributes of prior art fibrous webs and prior art plastic webs in a single structure without deleterious side effects.

The present invention has further relation to macroscopically expanded three-dimensional plastic webs having at least one substantially non-glossy visible surface.

The present invention has further relation to macroscopically expanded three-dimensional plastic webs exhibiting a non-glossy surface and a cloth-like or fiber-like tactile impression.

The present invention has further relation to the provision of method and apparatus for forming plastic webs exhibiting the aforementioned attributes.

BACKGROUND ART

It has long been known in the disposable absorbent bandage art that it is extremely desirable to construct absorptive devices, such as disposable diapers, sanitary napkins, incontinent devices, absorbent wound dressings, and the like, presenting a dry surface feel to the user to improve wearing comfort and to minimize the development of undesirable skin conditions due to prolonged exposure to moisture absorbed within the bandage. One viable prior art solution to the aforementioned problem is disclosed in U.S. Pat. No. 4,041,951 issued to Sanford on Aug. 16, 1977 and hereby incorporated herein by reference. The Sanford patent discloses a preferred disposable diaper structure comprising a substantially planar, moisture absorbent layer disposed between a soft topsheet and a moisture-resistant backing sheet. The nonwoven fibrous topsheet preferably comprises an integral structure containing a multiplicity of depressed areas which intimately contact the uppermost surface of a substantially planar, moisture absorbent layer. The nondepressed areas of the topsheet contact the wearer's skin in-use. In a particularly preferred embodiment, the nonwoven fibrous topsheet is comprised of a substantially hydrophobic material exhibiting wet resilience such that the topsheet tends to resume its substantially three-dimensional character upon removal of pressure applied against the topsheet by the body movements of the wearer. The nondepressed areas of the topsheet, which are of substantially the same density as the depressed areas, tend to isolate the wearer's skin from moisture contained within the moisture absorbent layer, thereby providing surface dryness and resistance to rewetting when the structure is temporarily subjected to pressure resulting from the wearer's body movements.

U.S. Pat. No. 3,814,101 issued to Kozak on June 4, 1974, attacks the problem of a wet topsheet in a manner slightly different from the use of hydrophobic nonwoven materials. Kozak suggests a topsheet of a nonfibrous, hydrophobic film which is provided with a plurality of valvular slits which restrict the reverse flow of liquid from the absorbent element of the device.

U.S. Pat. No. 3,929,135 issued to Thompson on Dec. 30, 1975, and hereby incorporated herein by reference, suggests a macroscopically expanded three-dimensinal topsheet comprised of liquid-impermeable material, but provided with tapered capillaries, said capillaries having a base opening in the plane of the topsheet and an apex opening remote from the plane of the topsheet, said apex opening being in intimate contact with the absorbent pad utilized in the disposable absorbent bandage.

As utilized herein, the term "macroscopically expanded", when used to describe three-dimensional plastic webs, ribbons and films, refers to webs, ribbons and films which have been caused to conform to the surface of a three-dimensional forming structure so that both surfaces thereof exhibit the three-dimensional pattern of said forming structure, said pattern being readily visible to the naked eye when the perpendicular distance between the viewer's eye and the plane of the web is about 12 inches. Such macroscopically expanded webs, ribbons and films are typically caused to conform to the surface of said forming structures by embossing, i.e., when the forming structure exhibits a pattern comprised primarily of male projections, by debossing, i.e., when the forming structure exhibits a pattern comprised primarily of female capillary networks, or by extrusion of a resinous melt directly onto the surface of a forming structure of either type. By way of contrast, the term "planar", when utilized herein to describe plastic webs, ribbons and films, refers to the overall condition of the web, ribbon or film when viewed by the naked eye on a macroscopic scale. In this context "planar" webs, ribbons and films may include webs, ribbons and films having fine scale surface aberrations on one or both sides, said surface aberrations not being readily visible to the naked eye when the perpendicular distance between the viewer's eye and the plane of the web is about 12 inches or greater. Planar plastic webs of the aforementioned type are known in the art.

The topsheet disclosed in the aforementioned Thompson patent allows the free transfer of fluids from the body into the absorbent element of the device while inhibiting the reverse flow of these fluids. This provides a relatively much drier surface in contact with the user than had been previously obtainable. However, experience has demonstrated that despite the highly effective fluid transfer and fluid isolation characteristics exhibited by plastic topsheets of the type generally disclosed in the Thompson patent and their proven compatibility with the wearer's skin, many users find it psychologically undesirable to employ a material which is perceivably plastic in contact with their skin. It is believed that this user reaction is due partly to the highly regulated tapered capillary pattern on the wearer-contacting surface of the topsheet and partly to the glossy appearance of The commonly assigned, co-pending U.S patent application of Clifford J. Radel and Hugh A. Thompson entitled RESILIENT PLASTIC WEB EXHIBITING FIBER-LIKE PROPERTIES AND METHOD AND APPARATUS FOR ITS MANUFACTURE, Ser. No. 206,410, filed Nov. 13, 1980, now U.S. Pat. No. 4,342,314 and hereby incorporated herein by reference, discloses an improved macroscopically expanded three-dimensional plastic web which eliminates the regulated pattern of tapered capillaries, as disclosed in the Thompson patent, while preserving the desirable fluid transport properties of the structure. The macroscopically expanded three-dimensional plastic web disclosed in the application of Radel et al. preferably exhibits a fine scale three-dimensional microstructure comprising a regulated continuum of capillary networks, preferably of steadily decreasing size, originating in and extending from one surface of said web and preferably terminating in the form of apertures in the opposite surface thereof to promote rapid liquid transport in the direction of decreasing capillary size. The web's fiber-like appearance is comprised of a continuum of fiber-like elements, each end of said fiber-like elements being interconnected to at least one other of said fiber-like elements. In a particularly preferred embodiment, the interconnected fiber-like elements are substantially non-aligned with respect to one another.

A typical capillary network in the Radel et al. structure comprises an uppermost capillary opening formed by a multiplicity of primary fiber-like elements interconnected to one another in the uppermost plane of the web. The opening may, if desired, be further subdivided into smaller capillary openings by secondary and tertiary fiber-like elements at planes located below the wearer-contacting surface of the web.

Each of the primary fiber-like elements exhibits a substantially uniform U-shaped cross-section along its length. Its cross-section comprises a base portion located in the wearer-contacting plane and a primary sidewall portion joined to each edge of said primary base portion and extending generally in the direction of the absorbent pad-contacting surface of the web. The secondary and tertiary fiber-like elements, when employed, are generally similar, but originate in planes below the wearer-contacting surface of the web. Because the plastic web of Radel et al. is comprised of a multiplicity of interconnected fiber-like elements rather than a continuous, regulated pattern of tapered capillaries, as disclosed in the Thompson patent, its appearance and tactile impression are generally perceived as more fiber-like.

In a particularly preferred embodiment of the Radel et al. invention, the web's visible surface (i.e., that surface which is generally observable from a perspective which is substantially perpendicular to the plane of the web) is also provided with a fine scale texture comprising a multiplicity of generally parallel V-shaped grooves to create a non-planar surface appearance in the web. The Radel et al. application suggests that the ridges and valleys formed in the plastic web by the V-shaped grooves in the forming structure tend to reduce the web's gloss.

The commonly assigned allowed U.S. patent application of Eugene R. Sorensen entitled DISPOSABLE DIAPER HAVING A TEXTURED THERMOPLASTIC FILM TOPSHEET, Ser. No. 225,944 filed on Jan. 19, 1981, now U.S. Pat. No. 4,327,730 and hereby incorporated herein by reference, likewise recognizes the perceived drawbacks associated with a glossy-appearing macroscopically expanded three-dimensional plastic web to be utilized in contact with the skin. Accordingly, the application of Sorenson discloses a macroscopically expanded three-dimensional plastic film provided with a surface texturing treatment. In a particularly preferred embodiment, the film is employed as a diaper topsheet. The texturing treatment preferably provides a multiplicity of "nubbles" integrally formed on at least one surface to "improve the tactile impression of the thermoplastic film and to reduce its gloss". The nubbles, which impart an irregular and unsmooth texture to the wearer-contacting surface of the topsheet, are small protuberances which project outwardly from the wearer-contacting surface of the topsheet. The number, size, and spacing of the nubbles may be varied within a critical range to give differing degrees of irregularity to the wearer-contacting surface. The nubbles are preferably spherical or spheroidal in cross-section, although it is suggested that other cross-sectional shapes may be used.

A preferred method for manufacturing such a topsheet is disclosed in the commonly assigned, co-pending U.S. patent application of Paul R. Louis, Eugene R. Sorenson and Thomas R. Ballard entitled METHOD AND APPARATUS FOR TEXTURING A THERMOPLASTIC FILM, Ser. No. 036,254, filed May 4, 1979 and issued on Mar. 31, 1981 as U.S. Pat. No. 4,259,286, said application and said patent being hereby incorporated herein by reference.

Briefly, Louis et al. employs a perforate tubular forming member having a multiplicity of particles affixed to its outermost or web-contacting surface. In a particularly preferred embodiment, the tubular member is coated with a mixture of said particles and epoxy, which epoxy may be electrostatically sprayed onto said tubular member and thereafter cured. As should be apparent from the foregoing description, the variability in size and spacing of the particles which form the nubbles in the plastic film processed on said tubular forming member is completely random, and will depend upon such factors as the uniformity in size and shape of the particles employed, the ratio of particles to epoxy, and the uniformity of the spraying techniques.

While the striation treatment disclosed in the aforementioned application of Radel et al. and the random particle treatment disclosed in the aforementioned applications of Louis et al. and Sorenson have in certain instances been employed to produce macroscopically expanded three-dimensional plastic webs exhibiting reduced gloss when compared to untreated prior art plastic webs, it is nonetheless an object of the present invention to accurately define the relevant criteria which must be satisfied to ensure that macroscopically expanded three-dimensional plastic webs which satisfy said criteria will exhibit a substantially non-glossy visible surface when the perpendicular distance between the viewer's eye and the plane of the web is about twelve inches or greater.

It is another object of the present invention to accurately define the relevant criteria which must be satisfied to ensure that macroscopically expanded three-dimensional plastic webs which satisfy said criteria will exhibit a substantially non-glossy visible surface and an improved cloth-like or fiber-like tactile impression.

It is another object of the present invention to provide macroscopically expanded, three-dimensional plastic webs which do in fact satisfy the aforementioned criteria.

It is still another object of the present invention to provide method and apparatus for producing plastic webs exhibiting the desirable characteristics described herein.

DISCLOSURE OF INVENTION

The present invention pertains, in a particularly preferred embodiment, to the provision of a macroscopically expanded three-dimensional plastic web having at least one substantially non-glossy visible surface. The substantially non-glossy visible surface exhibits a regularly spaced, microscopic pattern of surface aberrations which are not discernible when the perpendicular distance between the viewer's eye and the plane of the web is about 12 inches or greater. Each of the surface aberrations in said pattern are free of planar areas which are large enough to inscribe a four mil (i.e., 0.004 inch) diameter circle and are so spaced relative to all adjacent surface aberrations that the maximum diameter of any circle which can be inscribed on any planar surface intermediate said surface aberration and said adjacent surface aberrations is less than about four mils. Light incident upon the non-glossy visible surface of the web is substantially diffused into a multiplicity of directions by the aforementioned surface aberrations rather than being specularly reflected. Since the microscopic pattern of surface aberrations responsible for causing the diffuse reflection is not visually perceived by the observer under normal conditions, i.e., when the perpendicular distance between the viewer's eye and the plane of the web is about 12 inches or greater, macroscopically expanded three-dimensional plastic webs of the present invention are visually perceived as more cloth-like or fiber-like. The surface aberrations employed in the practice of the present invention may comprise protuberances projecting generally outwardly from the surface of said web or depressions projecting generally inwardly from the surface of said web.

Macroscopically expanded three-dimensional plastic webs of the present invention may also be made to exhibit a more cloth-like or fiber-like tactile impression by employing surface aberrations having an average amplitude of at least about 0.2 mils (i.e., 0.0002 inches), as measured from the top of said protuberance or the bottom of said depression, as the case may be, to the plane in which said aberration originates.

Preferred methods and apparatus for forming said macroscopically expanded three-dimensional plastic webs are also provided.

BRIEF DESCRIPTION OF THE DRAWINGS

While the specification concludes with claims particularly pointing out and distinctly claiming the present invention, it is believed the present invention will be better understood from the following description in which:

DETAILED DESCRIPTION OF THE INVENTION

Figure 1:
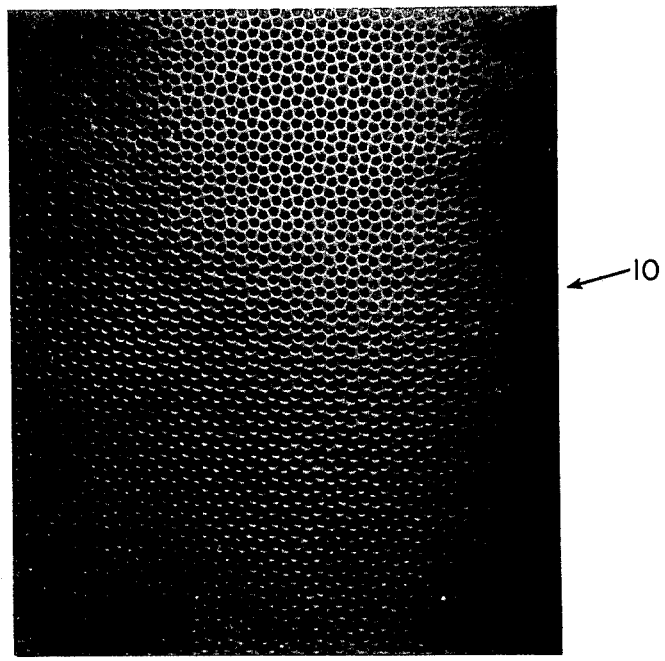
FIG. 1 is a plan view photograph of a macroscopically expanded, plain surfaced three-dimensional plastic web of the type generally disclosed in the aforementioned patent application of Radel et al., said web being shown approximately two times actual size.

It is generally known in the art that the appearance attributes of any object are related to the ways in which the object modifies the light that strikes it. The light can be modified spatially resulting in diffuse and specular reflection and/or diffuse and specular transmission. The light can also be modified spectrally (in color). As is pointed out, beginning at page 26, of a prior art reference entitled "The Measurements of Appearance" by Richard F. Hunter, John Wiley & Sons, New York, 1975, said text being hereby incorporated herein by reference, four major things can happen to light when it encounters an object: (1) specular reflection at the skin of the object (associated with gloss); (2) scattering within the material (associated with diffuse reflection and sometimes with diffuse transmission); (3) absorption within the material (largely responsible for color); and (4) specular transmission directly through the object, if it is more or less transparent (associated with clarity).

The present invention is concerned primarily with the first two phenomena, particularly the aspects of specular reflection and diffuse reflection. As utilized herein, specular reflection is considered to occur when a beam of light is reflected from a surface such that the angle of reflection is equal to the angle of incidence, and the component of its direction which is parallel to the plane of said surface remains unchanged. Diffuse reflection, on the other hand, comprises any reflection which is non-specular. An example of a surface exhibiting only specular reflection would be a perfect mirror. It will therefore be appreciated that nearly any real surface will exhibit both specular and diffuse reflection. The aforementioned reference of Hunter points out, beginning at page 26, that it is specular reflection which is responsible for the visible glossy appearance of a surface. With normal nonmetallic materials, the specularly reflected light is not changed in color. Accordingly, the highlights of the object being observed appear white, the color of the light source.

Conversely, if the surface of the object in question exhibits primarily diffuse reflection with respect to an incident beam of light, the surface tends to appear more mat. In general, the more diffuse the reflection from an opaque surface, the more mat will be the appearance. However, it has been observed that there does not appear to be any clearly defined point at which a surface ceases being perceived as glossy and suddenly appears to be mat. In fact, there seems to be a gradual transition in perception from glossy to mat with various stages in between typically being described with words like "satiny".

It is also generally known in the art that the amount of light reflected or transmitted by an object can vary as the direction of view is changed. Curves showing change of amount of reflectance or transmittance with change of angle of view are normally called goniophotometric curves. Such curves identify the properties of specimens responsible for gloss, haze, luster, and other geometric attributes. Basically, a goniophotometric curve is produced by fixing the light source at a specific angle and measuring the light reflected at different angles of view. A goniophotometric curve is typically plotted on a two-dimensional X-Y coordinate system by designating the reflectance factor as the Y-axis and the angle of reflection as the X-axis. The reflectance factor scale is typically plotted logarithmically. If, for example, such a curve showing the amount of light reflected in various directions with the specimen illuminated at an angle of 45° is plotted, a surface which is high in specular reflection will exhibit a very high peak value at an angle of −45° (i.e., the point at which the angle of incidence with the web and the angle of reflection from the web are equal) and a minimal area under the curve thus formed, while a surface which is very mat will generally exhibit little evidence of a peak and a rather large area under the curve. It will of course be recognized by those skilled in the art that if the reflectance factor scale were plotted linearly rather than logarithmically, then the total area under each curve would be similar. For example, a logarithmically plotted goniophotometric curve for a perfect mirror would be a substantially vertical spike at −45°, while the curve for a perfectly mat surface would be a substantially horizontal line extending generally parallel to the X-axis at a lesser amplitude than said vertical spike.

According to the teachings of Hunter, a variety of established methods of gloss measurement have been developed over the years due to the necessity of measuring different aspects of reflection in order to duplicate, as far as possible, the different visual gloss grading procedures which are possible with the human eye. A more complete description of these generally accepted methods may be found in the aforementioned reference of Hunter, beginning at page 71.

Hunter expressly recognizes the relatively limited abilities of instruments typically employed when compared to the human eye. He suggests, at page 76, that the human eye has a higher resolving power than do most reflectance measuring instruments. According to Hunter, the normal human eye can see two lines as being separate when they are only 0.01° apart, while photometric measurements of reflectance are typically limited to receptor field angles about 100 times as large. Furthermore, the requirement for flat test surfaces for narrow-angle measurements of high gloss is very important when dealing with quantitative instrument measurements because an instrument cannot differentiate between a low reflectance rating due to poor imge-reflecting quality of the specimen and a low reference rating caused by surface curvature that has directed the specularly reflected light beam improperly. The eye, however, can readily distinguish between these effects, since specimen nonflatness distorts, but does not destroy, the visual images reflected in its surface.

Accordingly, attempts to quantify gloss utilizing prior art measuring techniques and to meaningfully correlate such quantitative measurements with a human observer's visual perception have not been completely successful. This is believed due to the fact that such prior art techniques take into consideration only one of the criteria which must be met to provide a surface which is perceived by the human eye as substantially non-glossy.

It has, in reducing the present invention to practice, been confirmed that the ability of a surface to exhibit primarily diffuse reflection is a necessary condition to minimize visually perceived gloss. However, the ability of a surface to exhibit diffuse reflection is not, in and of itself, a sufficient criteria to create the visual perception of a mat surface. A second criteria which must also be met is that the diffusing pattern must be sufficiently fine that it is nondiscernible to the naked eye of the observer under normal circumstances. If the pattern is discernible by the naked eye, then the surface will be visually perceived as a basically glossy surface with disruptions on it.

Experience with macroscopically expanded three-dimensional plastic webs of the type disclosed in the aforementioned patent applications of Radel et al. and Sorenson has demonstrated that gloss is visually perceived either: (a) when there is no pattern of surface aberrations to diffusely reflect the incident light; or (b) when the pattern of surface aberrations is discernible to the naked eye. Conversely, experience in reducing the present invention to practice has demonstrated that when the pattern of surface aberrations causes the surface to exhibit primarily diffuse rather than specular reflection and the pattern of surface aberrations is of a scale fine enough that it is not discernible to the naked eye under normal use conditions, then the surface is visually perceived as being mat.

Exemplary embodiments of macroscopically expanded three-dimensional plastic webs of the type disclosed in the aforementioned patent applications of Radel et al. and Sorenson are disclosed in FIGS. 1–4 and 5–8, respectively, while exemplary embodiments of macroscopically expanded three-dimensional plastic webs of the present invention are disclosed in FIGS. 9 through 16.

FIGS. 1, 2, 5, 6, 9, 10, 13 and 14 are all plan view photographs taken with the incident light forming an angle of approximately 20° with the plane of the webs. Thus, for the plan view photographs described above the angle formed between the camera lens and the incident light is approximately 70°. As pointed out earlier herein, maximum specular reflection would normally occur when the angle of light reflectance is equal to the angle of light incidence. Accordingly, FIGS. 3, 4, 7, 8, 11, 12, 15 and 16 are photographs taken when the sample has been repositioned to make the camera coincide with the angle of reflectance of the incident light to illustrate the condition existing at the point of maximum specular reflection. The incident light angle for these photographs was 55° with respect to the plane of the web, and the angle of reflectance, i.e., the angle at which the camera was positioned, was −55° with respect to the plane of the web.

The webs disclosed in FIGS. 1–16 all exhibit a similar macroscopically expanded three-dimensional pattern. The forming structure utilized was generally similar to that disclosed in FIG. 20 and was comprised of a stack of identical photoetched laminae, each having a multiplicity of irregularly shaped pentagonal apertures therein. The maximum dimension of said pentagonally shaped apertures was approximately 35 mils (i.e., 0.035 inches). Each lamina exhibited a thickness of approximately 10 mils (i.e., 0.010 inches). Five such lamina were superposed with their pentagonally shaped apertures in vertical alignment to provide a forming structure exhibiting a multiplicity of pentagonally shaped capillary networks having sidewalls oriented substantially perpendicular to the plane of plastic webs processed thereon. The laminae were secured to one another to form an integral structure generally in accordance with the teachings of the aforementioned patent application of Radel et al.

The uppermost lamina of the forming structure utilized to produce the macroscopically expanded three-dimensional plastic web 10 disclosed in FIGS. 1–4 was left untreated, i.e., no pattern of surface aberrations was provided on its uppermost surface.

Figure 2:
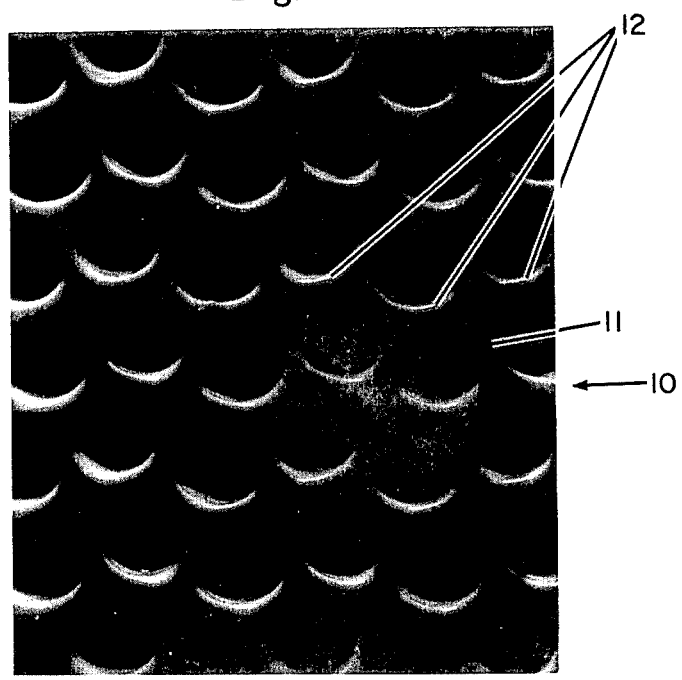
FIG. 2 is a photograph generally similar to that of FIG. 1, said web being shown approximately 18 times actual size.
Figure 3:
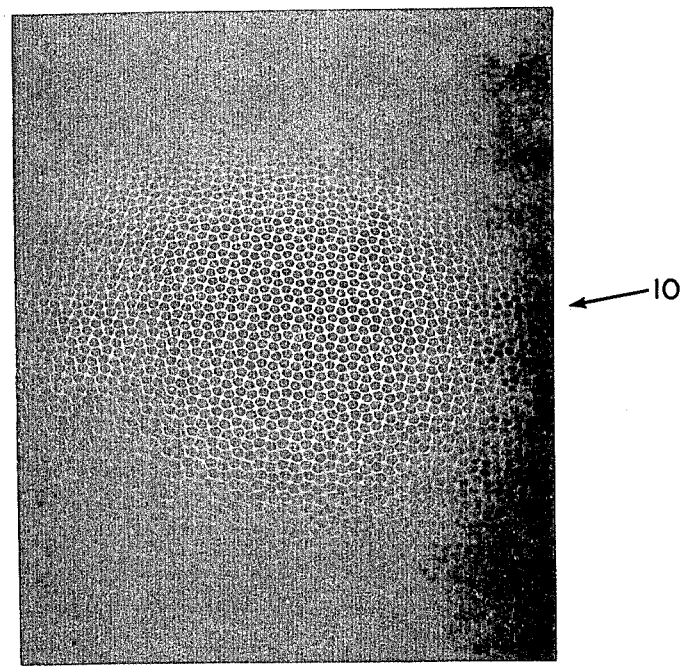
FIG. 3 is a photograph of the web shown in FIGS. 1 and 2 taken at an angle of approximately 55° with respect to the plane of said web, said web being shown approximately two times actual size.
Figure 4:
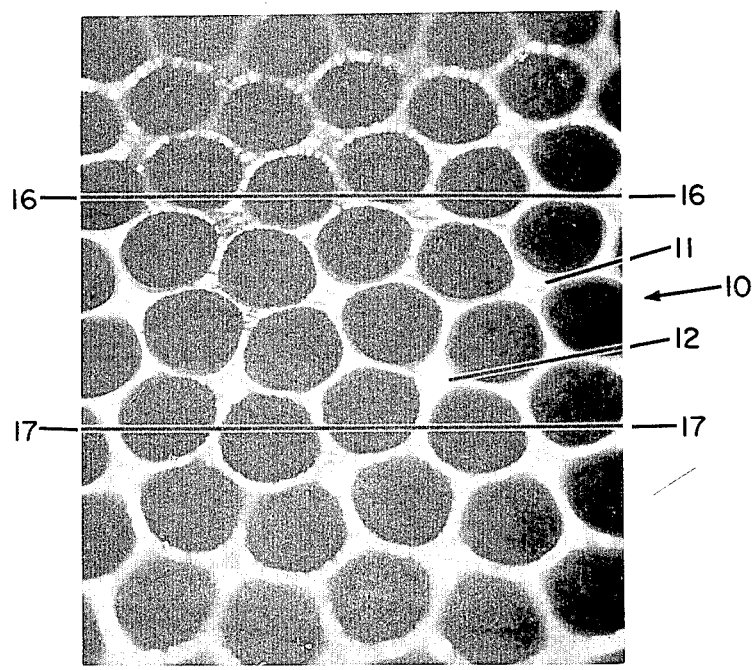
FIG. 4 is a photograph generally similar to that of FIG. 3, said web being shown approximately 18 times actual size.
Figure 5:
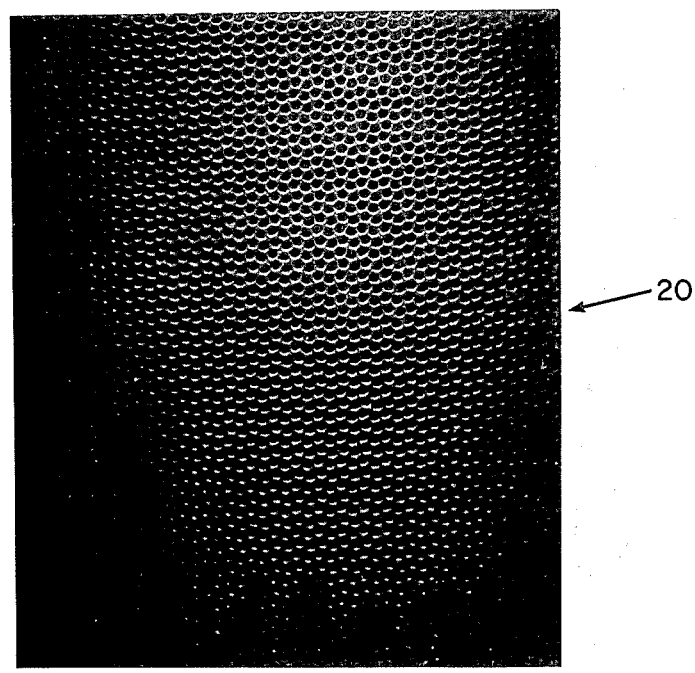
FIG. 5 is a plan view photograph of a macroscopically expanded three-dimensional plastic web of the type generally disclosed in FIGS. 1-4, but incorporating a pattern of irregularly sized and irregularly spaced nubbles of the type disclosed in the aforementioned patent application of Sorenson on its visible surface, said web being shown approximately two times actual size.

The web 10 is shown about two times actual size in FIGS. 1 and 3 to lend some perspective to the fineness of the three-dimensional pattern, and about 18 times actual size in FIGS. 2 and 4 to clarify the gloss phenomenon. Due to the limitations inherent in photographic techniques, the gloss phenomenon perceived by the human eye when examining the actual samples is not readily apparent from an examination of the photographs taken at the lower scale magnification.

While the highly enlarged plan view photograph of FIG. 2 shows only isolated gloss highlights 12 on the web's visible surface 11, the photograph of FIG. 4, which coincides with the angle of reflectance for the incident light exhibits a substantially continuous gloss highlight on the web's visible surface. In this regard it should be noted that only those portions of FIG. 4 located intermediate view lines 16—16 and 17—17 are in proper focus due to the angular orientation of the web 10 with respect to the camera. It is this specularly reflected light which is visually perceived as gloss by the observer when the web 10 is subjected to normal use.

The forming structure utilized to produce the macroscopically expanded three-dimensional plastic web 20 disclosed in FIGS. 5–8 was treated with an epoxy grit mixture generally in accordance with the teachings of the aforementioned patent applications of Sorenson and Louis et al. In particular, a mixture comprised of 70 percent No. 400 Grit and 30 percent No. 325 Grit was mixed with a powdered epoxy in a ratio of approximately 3:2 (grit:epoxy) and sprayed as a powder onto the uppermost surface of the electrostatically charged forming structure. Once deposited on the surface of the forming structure the mixture of grit and epoxy were baked generally in accordance with the teachings of the aforementioned patent application of Louis et al. to secure the grit permanently in place.

Figure 6:
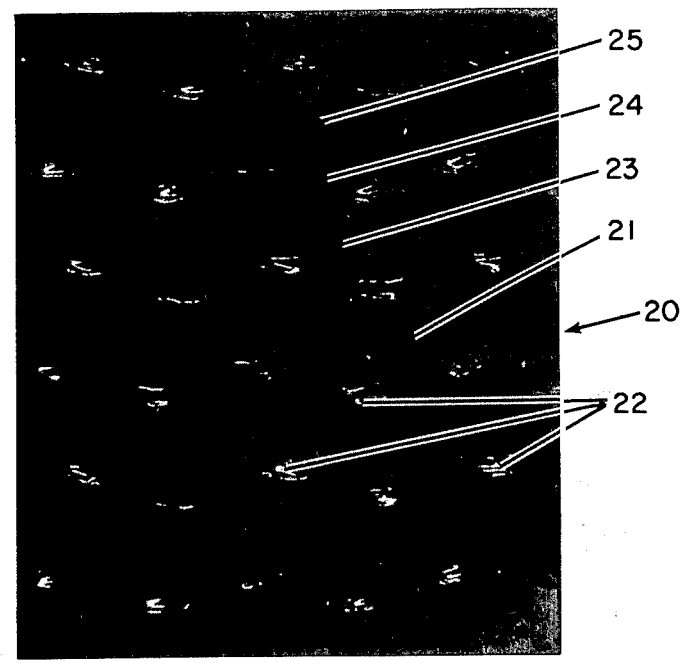
FIG. 6 is a photograph generally similar to that of FIG. 5, said web being shown approximately 18 times actual size.
Figure 7:
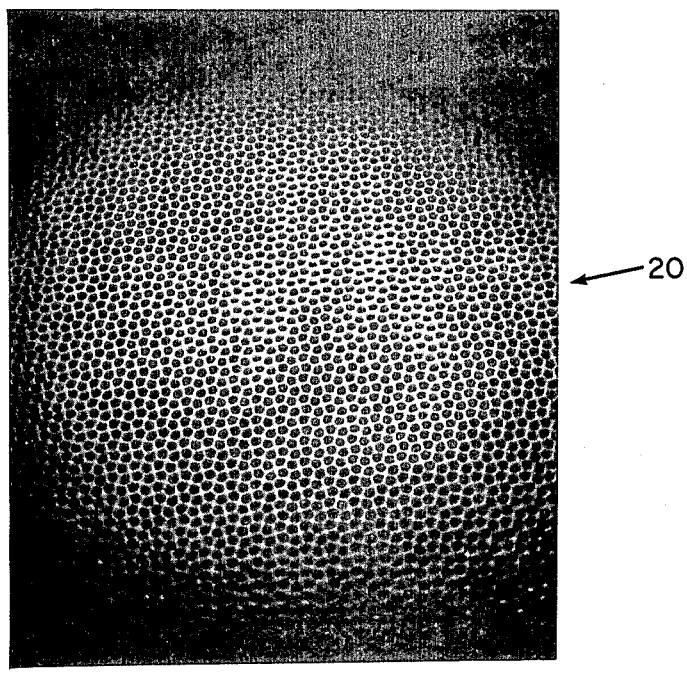
FIG. 7 is a photograph of the web generaly shown in FIGS. 5 and 6 taken at an angle of approximately 55° with respect to the plane of said web, said web being shown approximately two times actual size.
Figure 8:
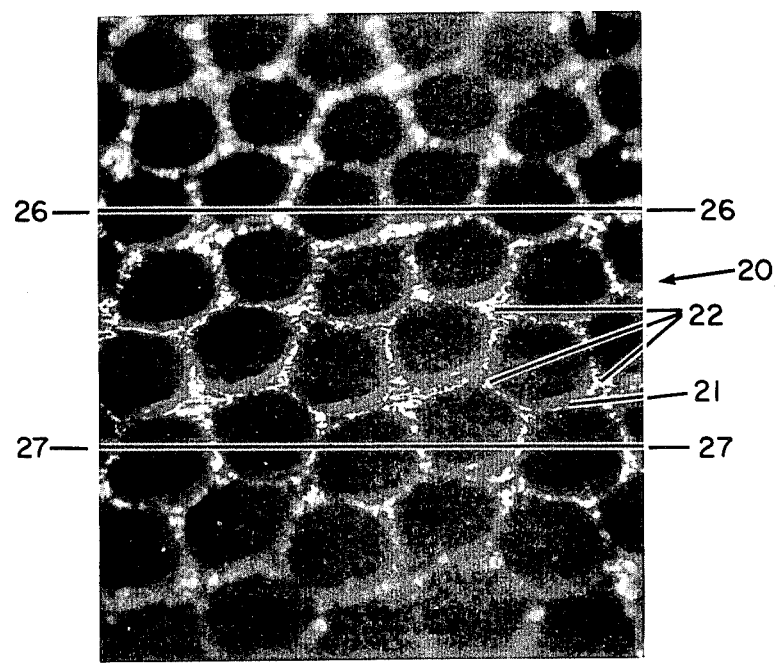
FIG. 8 is a photograph generally similar to that of FIG. 7, said web being shown approximately 18 times actual size.
Figure 9:
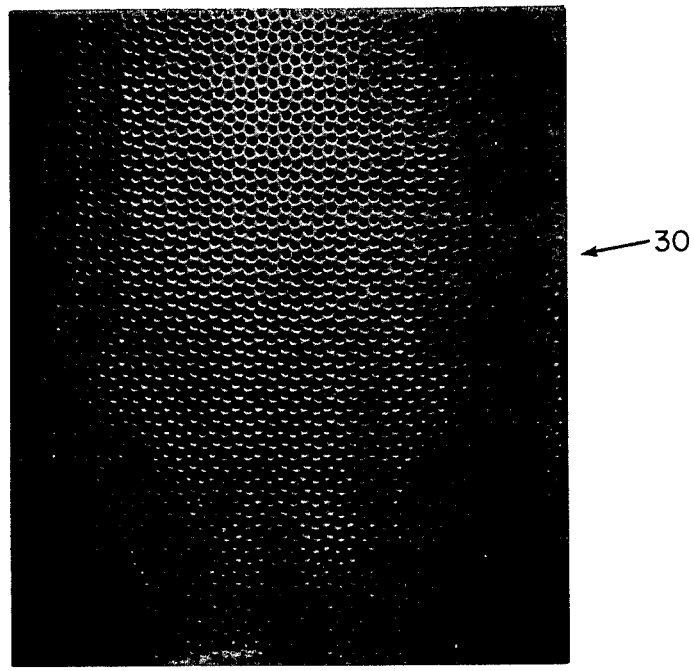
FIG. 9 is a plan view photograph of a preferred embodiment of a macroscopically expanded three-dimensional web of the present invention, said web being shown approximately two times actual size.

As can be seen in FIG. 6, the visible surface 21 of web 20 is provided with a multiplicity of irregularly sized and irregularly spaced nubbles, e.g., nubbles 23, 24, 25. As with the web 10, shown in FIGS. 1–4, the plan view photograph of FIG. 6 shows only isolated gloss highlights 22 on the web's visible surface 21, while the photograph of FIG. 8, which coincides with the angle of reflectance of the incident light, exhibits much more extensive gloss highlights on the web's visible surface. Nonetheless, there is generally less visually perceived gloss under normal use conditions with webs of the type disclosed in FIGS. 5–8 than with webs of the type disclosed in FIGS. 1–4 due to the presence of the nubbles, e.g., nubbles 23, 24, 25. As with FIG. 4, only those portions of FIG. 8 located intermediate view lines 26—26 and 27—27 are in proper focus due to the angular orientation of the web 20 with respect to the camera.

Figure 17:
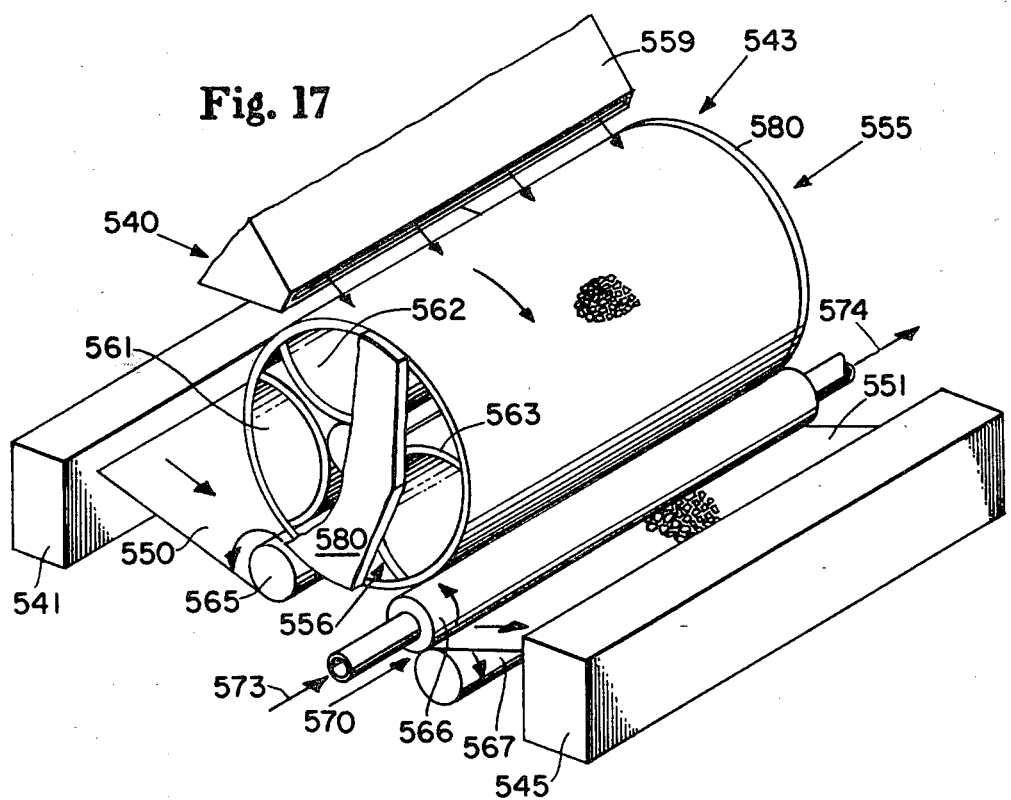
FIG. 17 is a simplified schematic illustration of a preferred method and apparatus used to produce a macroscopically expanded, three-dimensional plastic web of the present invention.

The web 30 shown in FIGS. 9–12 is a preferred embodiment of the present invention produced utilizing a one-sided forming process of the type generally disclosed in FIG. 17. The uppermost lamina of the forming structure utilized to produce the macroscopically expanded three-dimensional plastic web 30 disclosed in FIGS. 9-12 was provided with a microscopic pattern of regularly spaced surface aberrations generally similar to surface aberrations 160 disclosed in FIG. 20. The aberrations, which comprised protuberances projecting generally outwardly from the surface of the web, were circular in cross-section, as measured in a plane oriented perpendicular to their amplitude, i.e., a plane parallel to the surface of said web. They had an overall cross-sectional diameter of approximately four mils (i.e., 0.004 inches) and were arranged in a hexagonally close packed pattern with a four mil (i.e., 0.004 inch) center-to-center spacing between adjacent surface aberrations. The average amplitude of the surface aberrations was approximately 0.3 mils (i.e., 0.0003 inches). The surface aberrations were provided in the uppermost lamina of the forming structure after the pentagonally shaped apertures had been provided therein by a secondary photoetching treatment of the type generally disclosed in the aforementioned patent application of Radel et al.

The amplitude of the surface aberrations referred to throughout the present specification and claims is preferably measured using a high powered microscope which enables the operator to measure distance perpendicular to the plane of the sample as a function of focus. In particular, this method employs a top lighted metallurgical microscope with a calibrated focusing wheel. While the degree of magnification is typically adjustable on these units, a magnification of 400x has been found to provide a good compromise between depth of focus and viewing area.

Samples of the web to be measured are preferably prepared by cutting a rectangular section approximately ½ inch by 1½ inches from the web. These samples are then mounted on individual microscope slides using double-sided tape with their visible surface upwardly oriented. The visible surface of each sample is preferably darkened with a black felt tip marker. Since webs of the present invention may be completely transparent, completely opaque, or anywhere between these two extremes, the ink applied by the felt tip marker permits accurate amplitude measurement regardless of the degree of transparency or opacity of the particular web being measured. Darkening in the aforementioned manner with a felt tip marker provides improved contrast between the uppermost surface of the aberration and the plane of origination adjacent the aberration to be measured. Due to the tendency of the ink to run from the uppermost surface of the aberration, the uppermost surface will normally appear somewhat lighter under the microscope, while the plane of origination, which is generally perceived as a valley, will appear generally darker in color. A Sanford Sharpie No. 3000 black felt tip marker, such as is available from Sanford Corporation of Bellwood, Ill., may be employed for the aforementioned purpose.

Once the web sample has been prepared, the following procedure is preferably carried out:

1. Place the prepared sample on the microscope with the visible surface of the sample oriented toward the lens.

2. Focus on the top of a particular surface aberration and then on the plane of origination adjacent said aberration to identify distinguishing features to be used in determining focus. As mentioned earlier herein, the uppermost surface of the aberration will normally appear somewhat lighter in color, while the plane of origination adjacent the aberration will appear generally darker in color.

3. Adjust the focus of the microscope until it is above the plane of the uppermost surface of the particular surface aberration to be measured.

4. Turn the focus wheel in one direction only until the uppermost surface of the particular surface aberration just comes into focus. Stop turning at this point and record the reading from the focus wheel.

5. Continue turning in the same direction until the plane of origination adjacent said aberration just comes into focus. Stop turning the focus wheel and again record the reading from the focus wheel.

6. The difference between these two readings on the focus wheel represents the amplitude of the particular surface aberration from its plane of origination. Since the focus wheel is calibrated the distance of travel can readily be converted into mils.

The aforementioned procedure can also be used in situations wherein the surface aberration comprises a depression rather than a protuberance, the readings preferably being taken first in the plane of origination and then at the point of maximum amplitude.

When using the aforementioned measurement method, it is preferred that the focusing be accomplished by turning the focus wheel in one direction only. This eliminates any end play in the focus wheel mechanism which could be significant when compared to the values being measured. It should also be noted that the leading edge of the focus field is preferably used when the measurements described above are recorded in order to minimize the effect of a finite, i.e., greater than zero, depth of field. This is accomplished by stopping and recording the reading on the focus wheel when the surface in question just comes into focus, rather than at the point corresponding to the middle of the focus field or the point at which the trailing image is about to go out of focus. When this is done for both the first and the second readings, the effect of a finite depth of field is substantially eliminated from the amplitude measurement.

While nearly any microscope with top light capability, magnification power of 400x (or greater) and a calibrated focusing wheel may be utilized to perform the above measurements, particularly good results have been obtained utilizing an ausJena Neophot 21 metallurgical microscope set at 400x. This particular equipment is manufactured in Jena, East Germany and is distributed in the U.S.A. by the Leco Corporation of Warrendale, Pa. If desired, the unit may also be equipped with a television camera and video monitor for easier viewing.

To ensure that the amplitude determination made utilizing the foregoing technique is representative for the entire surface of the web sample, each of the ½ inch by 1½ inch web samples is preferably measured in at least 16 individual locations selected at random. The average amplitude for any given sample is computed by calculating the arithmetic average of all measurements taken from a given web sample. Thus, the average amplitudes reported throughout the present specification and claims represent the arithmetic average for the sample, as determined by the foregoing technique.

Figure 10:
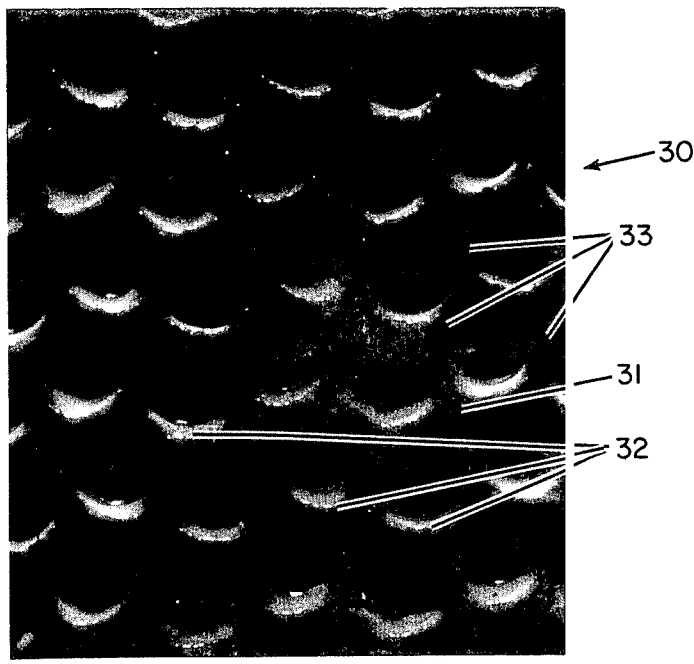
FIG. 10 is a photograph generally similar to that of FIG. 9, said web being shown approximately 18 times actual size.
Figure 11:
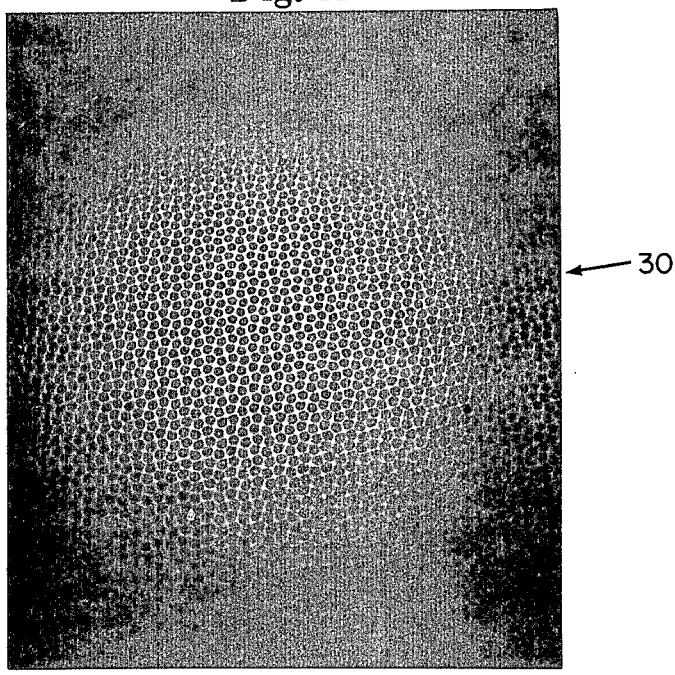
FIG. 11 is a photograph of the web generally shown in FIGS. 9 and 10 taken at an angle of approximately 55° with respect to the plane of said web, said web being shown approximately two times actual size.
Figure 12:
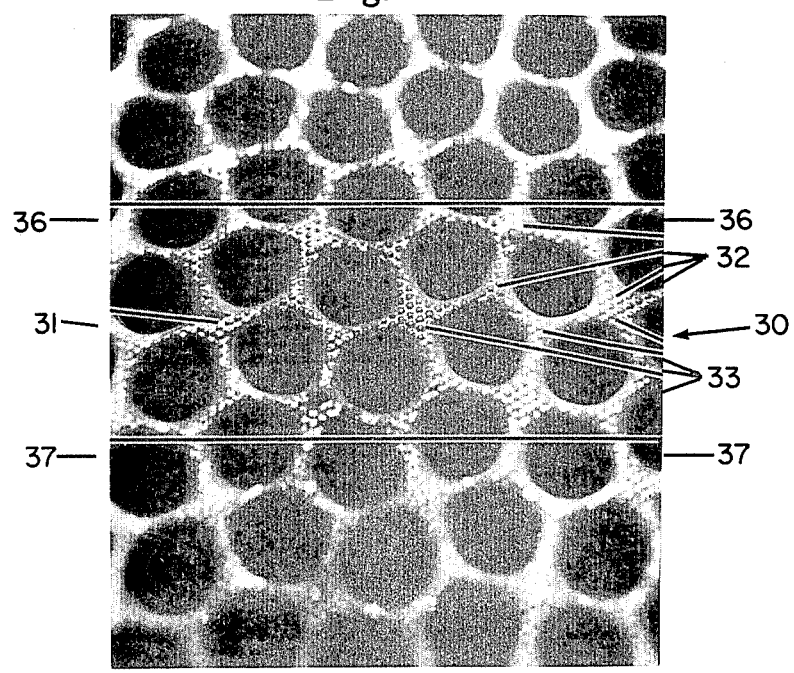
FIG. 12 is a photograph generally similar to that of FIG. 11, said web being shown approximately 18 times actual size.
Figure 13:
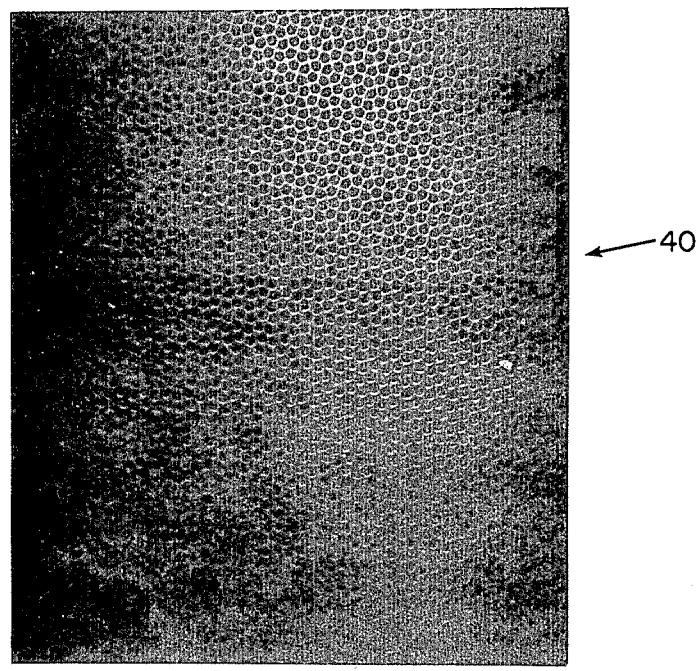
FIG. 13 is a plan view photograph of another preferred embodiment of a macroscopically expanded three-dimensional plastic web of the present invention, said web being shown approximately two times actual size.

As can be seen in FIG. 12, the visible surface 31 of the web 30 formed on the structure described earlier herein is provided with a multiplicity of regularly sized and spaced surface aberrations 33 corresponding to the surface aberrations on the forming structure. As with the webs 10 and 20 shown in FIGS. 1-4 and 5-8, respectively, the plan view photograph of FIG. 10 shows a number of isolated gloss highlights 32 on the web's visible surface 31. However, unlike the photographs of FIGS. 4 and 8 the photograph of FIG. 12, which coincides with the angle of reflectance of the incident light, exhibits only slightly more extensive gloss highlights on the web's visible surface than the plan view photograph of FIG. 10. Accordingly, when the web is subjected to normal use, the microscopic pattern of surface aberrations serves to diffusely deflect a substantial portion of the light incident upon the web's visible surface. Furthermore, because the pattern of surface aberrations causing diffuse reflection of the incident light cannot be discerned when the perpendicular distance between the observer's eye and the plane of the web is about 12 inches or greater, the web is perceived as substantially non-glossy. Finally, because the average amplitude of the surface aberrations 33 is about 0.3 mils (i.e., 0.0003 inches), the tactile impression exhibited by the web is generally perceived to be more cloth-like or fiber-like than for webs of the type illustrated in FIGS. 1-8.

Figure 21:
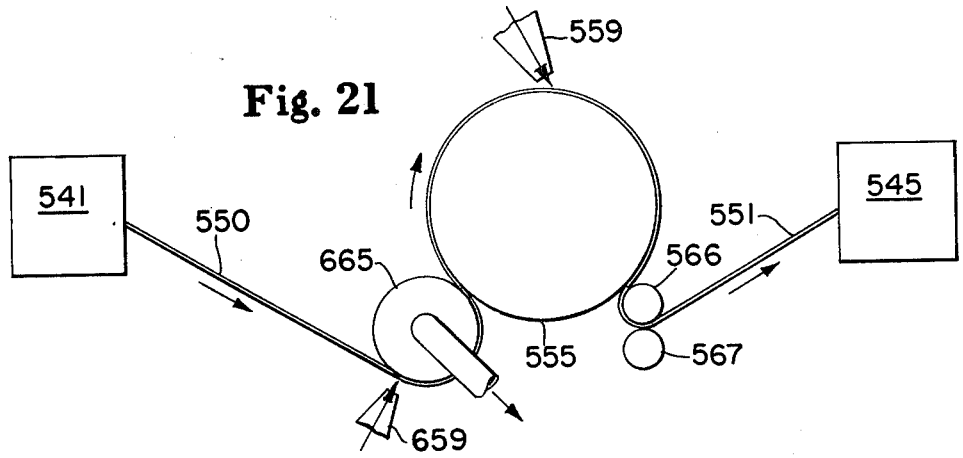
FIG. 21 is a simplified schematic illustration of a preferred two-sided film forming process of the present invention.

The macroscopically expanded three-dimensional plastic web 40 generally disclosed in FIGS. 13-16 is another preferred embodiment of the present invention produced utilizing a two-sided forming process of the type generally shown in FIG. 21. The web 40 was processed by subjecting its visible surface 41 to suction while the web was supported at an elevated temperature on a woven wire mesh forming structure. The wire mesh was woven from filaments having a diameter of about 1.6 mils (i.e., 0.0016 inches) in a square weave pattern and exhibited a mesh count of approximately 245 filaments per lineal inch by 245 filaments per lineal inch. The web was thereafter macroscopically expanded on a plain-surfaced three-dimensional forming structure. As a result, the visible surface of the web 40 exhibits a microscopic pattern of regularly spaced surface aberrations 43 which, in this case, comprise depressions corresponding to the knuckles of the aforementioned woven wire mesh forming structure.

Figure 14:
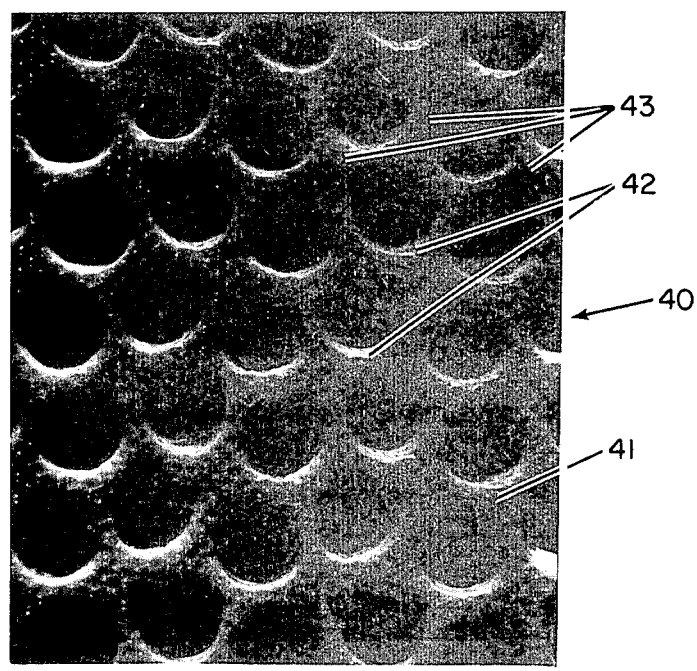
FIG. 14 is a photograph generally similar to that of FIG. 13, said web being shown approximately 18 times actual size.
Figure 15:
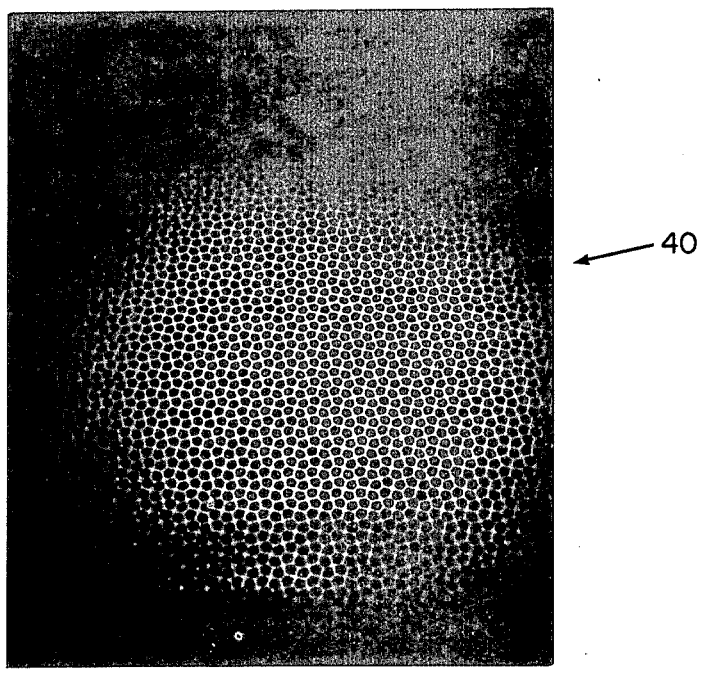
FIG. 15 is a photograph of the web generally shown in FIGS. 13 and 14 taken at an angle of approximately 55° with respect to the plane of said web, said web being shown approximately two times actual size.

As can be seen in the greatly enlarged plan view photograph of FIG. 14, only isolated gloss highlights 42 are observable on the web's visible surface 41.

Figure 16:
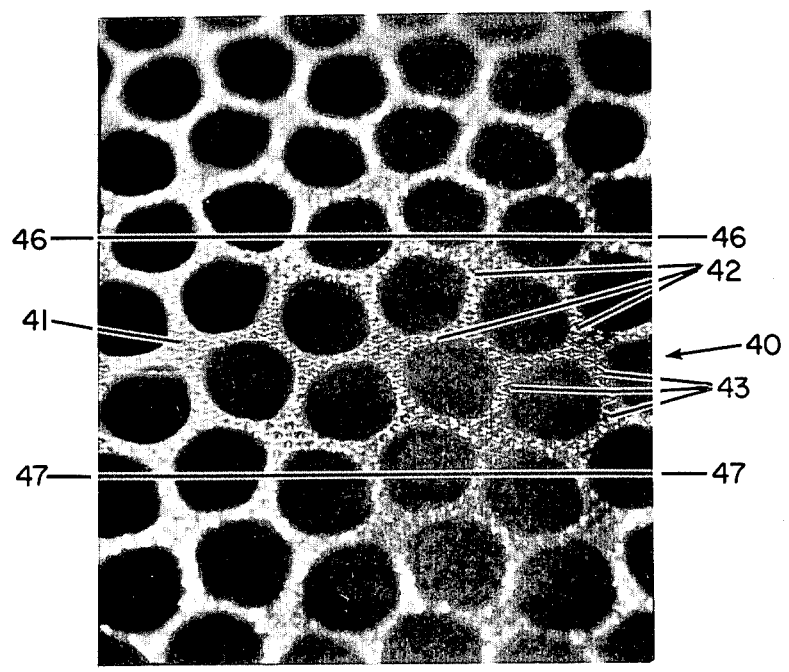
FIG. 16 is a photograph generally similar to that illustrated in FIG. 15, said web being shown approximately 18 times actual size.

The reduction in gloss is even more apparent from the photograph of FIG. 16, which coincides with the angle of reflectance of the incident light. FIG. 16 exhibits only a limited number of very small gloss highlights 42 due to the fine scale pattern of surface aberrations 43 which serve to diffusely reflect the incident light. When the web 40 is subjected to normal use, the microscopic pattern of regularly spaced surface aberrations 43 is not discernible when the perpendicular distance between the observer's eye and the plane of the web is about 12 inches or greater. This lack of visual discernibility can readily be verified from an inspection of FIGS. 13 and 15 which are shown approximately two times actual size.

Because the average amplitude of the surface abberrations 43 on web 40 is about 0.3 mils (i.e., 0.0003 inches), the web 40 exhibits a tactile impression generally similar to that of the web 30 disclosed in FIGS. 9-12.

From the foregoing it is apparent that the present invention has identified two key criteria which must be simultaneously satisfied for a surface which is normally glossy, e.g., an opaque plastic web, to appear mat under normal use circumstances. First, the surface must diffusely reflect rather than specularly reflect a substantial portion of the light incident upon it, and second, the regularly spaced, microscopic pattern of surface aberrations utilized to diffuse the light, which must be present throughout the visible surface of the web, must not be discernible to the naked eye when the web or the object embodying the web is subjected to normal use.

Applying these criteria to substantially opaque macroscopically expanded three-dimensional plastic webs which may be employed as alternatives for cloth and fibrous structures which contact the wearer's skin, as well as for new product applications, it has been observed that unless a person holding an object in his or her hands is attempting to examine the nature of the object in detail, the hands are normally maintained a distance of at least about twelve inches or more away from the eyes. Based upon this observation, it has been determined that a macroscopically expanded three-dimensional plastic web can be provided with a substantially non-glossy visible surface when the visible surface of the web is made to exhibit a regularly spaced, microscopic pattern of surface aberrations which are not discernible to the normal naked eye when the perpendicular distance between the observer's eye and the plane of the web is about 12 inches or greater.

The regularity of pattern and spacing, which is not embodied in the macroscopically expanded three-dimensional plastic web 20 disclosed in FIGS. 5-8, is necessary to ensure that all portions of the web's visible surface exhibit the desired characteristics. If substantially less than the entire visible surface of the web exhibits the desired characteristics, gloss will be perceived in those areas which fail to comply, and the desired cloth-like or fiber-like impression may be lost with respect to the entire web.

It has further been determined in reducing the present invention to practice that in order to provide primarily diffuse rather than specular reflection, each of the aforementioned surface aberrations must be substantially free of planar areas which are large enough to inscribe a four mil (i.e., 0.004 inch) diameter circle, and must be so spaced relative to all adjacent surface aberrations that the maximum diameter of any circle which can be inscribed on any planar surface intermediate said surface aberration and said adjacent surface aberrations is less than about four mils (i.e., 0.004 inches). These criteria are not satisfied by either of the web embodiments disclosed in FIGS. 1-4 or 5-8.

A check for the presence of planar areas which are large enough to inscribe a four mil diameter circle on the surface of a particular web sample may be made by orienting the surface or portion thereof to be examined substantially perpendicular to the viewing angle of a top lighted metallurgical microscope of the type described earlier herein in connection with measuring the amplitude of the surface aberrations. Samples of the web to be measured are prepared in a manner similar to that described in connection with the aforementioned amplitude measurements. The visible surface of each sample is preferably darkened with a black felt tip marker to permit accurate measurement regardless of the degree of transparency or opacity of the web.

Using a high magnification, preferably 1000x, a plane may be defined as any area which appears simultaneously in focus. The previously described four mil diameter circle can be inscribed in the particular planar area being examined if the boundary of the four mil diameter circle and all of the area contained therein appear to be simultaneously in focus. This examination is most easily facilitated by coupling a television camera and video monitor with a correspondingly enlarged four mil diameter circle overlaid on the screen of the video monitor to the microscope. Because the depth of field for focusing is shallow with a magnification of 1000x, it can be seen that movement of ±0.02 mils (±0.00002 inches) from a focused position is more than sufficient to render total obscurity of all details being examined due to blurring. Since naturally occuring surface imperfections on smooth web samples which do not exhibit surface aberrations of the type herein disclosed generally fall within the foregoing range, this level of accuracy is considered adequate for determining whether or not a four mil diameter circle may be inscribed in the area being examined.

It has been further learned in practicing the present invention to advantage that the aforementioned surface aberrations may comprise protuberances projecting generally outwardly from the surface of the web or depressions projecting generally inwardly from the surface of the web.

Unexpectedly, it has also been learned that a more cloth-like or fiber-like tactile impression can be obtained in macroscopically expanded three-dimensional webs of the present invention when the surface aberrations described earlier herein have an average amplitude of at least about 0.2 mils (i.e., 0.0002 inches), most preferably at least about 0.3 mils (i.e., 0.0003 inches), as measured perpendicularly from the top of the protuberance or the bottom of the depression, as the case may be, to the plane in which said surface aberration originates.

For persons having normal vision, it has been determined that in order to maintain nondiscernibility of the pattern of surface aberrations when the perpendicular distance between the viewer's eye and the plane of the web is about 12 inches, the maximum dimension of any of said surface aberrations should be less than about 6 mils (i.e., 0.006 inches), as measured in a plane substantially perpendicular the amplitude of said surface aberration, i.e., a plane substantially parallel to the surface of said web.

The macroscopically expanded three-dimensional plastic webs disclosed in FIGS. 9–12 and 13–16, which are preferred embodiments of the present invention, satisfy the aforementioned criteria for a substantially non-glossy visible surface as well as the aforementioned criteria for a more cloth-like or fiber-like tactile impression.

A particularly preferred continuous forming process which may be employed in practicing the present invention on webs comprised of plastic film and having a substantially uniform planar thickness of about two mils or less, as measured prior to any macroscopic expansion thereof, is schematically illustrated in FIG. 17. This process is generally described in commonly assigned U.S. Pat. No. 4,151,240 issued to Malcolm B. Lucas and Robert H. Van Coney on Apr. 24, 1979, said patent being hereby incorporated herein by reference. The particularly preferred apparatus 540 shown in FIG. 21 includes constant tension film supply means 541, debossing and perforating means 543, and constant tension film forwarding and winding means 545. The frame, bearings, supports and the like which must necessarily be provided with respect to the functional members of apparatus 540 are not shown or described in detail in order to simplify and more clearly depict and disclose the present invention, it being understood that such details would be obvious to persons of ordinary skill in the art of designing plastic film converting machinery.

Briefly, apparatus 540, FIG. 17, comprises means for continuously converting a planar ribbon of thermoplastic film 550 into a macroscopically expanded three-dimensional film 551 by directing hot air jets against one surface of the film while applying vacuum adjacent the opposite surface of the film, and while maintaining sufficient control of the film to substantially obviate wrinkling and/or macroscopically distending the film. Thus, as will be more fully described hereinafter, the apparatus 540 comprises means for maintaining constant machine direction tension in the film both upstream and downstream of a zone where the temperature is greater than the thermoplastic temperature of the film, but in which zone there is substantially zero machine direction and cross-machine direction tension tending to macroscopically distend the film. The aforementioned upstream and downstream tension is required to control and smooth the running ribbon of thermoplastic film. The zero tension zone results from the film in the zone being at a sufficiently high temperature to enable debossing and, if desired, perforating or aperturing it through the use of heat and vacuum. The perforations shown in FIG. 17 are greatly enlarged to enable visually perceiving the nature of the difference between the imperforate planar film 550 and the resulting macroscopically expanded three-dimensional film 551, as more fully described hereinafter.

As can be seen in FIG. 17, the debossing and perforating means 543 includes a rotatably mounted debossing/perforating cylinder 555 having closed ends 580, a nonrotating triplex vacuum manifold assembly 556 and hot air jet means 559. The triplex vacuum manifold assembly 556 comprises three manifolds designated 561, 562 and 563. Also shown in FIG. 17 is a freely rotatable lead-on idler roll 565, a power rotated lead-off/chill roll 566, and a soft-faced (e.g., low density neoprene) roll 567 which is driven with the chill roll.

Briefly, by providing means (not shown) for independently controlling the degree of vacuum in the three vacuum manifolds, a thermoplastic ribbon of film running circumferentially about a portion of debossing-/perforating cylinder 555 is sequentially subjected to a first level of vacuum by manifold 561, a second level of vacuum by manifold 562, and a third level of vacuum by manifold 563. As will be described more fully hereinafter, vacuum applied to the film by manifold 561 enables maintaining upstream tension in the film, vacuum applied by manifold 562 enables three-dimensionally debossing and perforating the film when hot air is directed radially inwardly against the film, and vacuum applied by manifold 563 cools the film to below its thermoplastic temperature and enables establishing downstream tension therein. If desired, the film contacting surface of the debossing/perforating cylinder 555 may be preheated prior to reaching vacuum manifold 562 by means well known in the art (and therefore not shown) to facilitate better conformance of plastic films comprised of flow-resistant polymers to the forming structure during the debossing and perforating operation. The nip 570 intermediate chill roll 566 and the soft-faced roll 567 is only nominally loaded to avoid ironing out the three-dimensional debossments which are formed in the film in the aforementioned manner.

However, even nominal pressure in nip 570 helps the vacuum applied by manifold 563 to isolate downstream tension (i.e., roll winding tension) from the debossing-/perforating portion of the debossing/perforating cylinder 555, and enables the nip 570 to peel the three-dimensionally debossed and perforated film from the debossing/perforating cylinder 555. Moreover, while ambient air passing through the film as it is drawn by vacuum into manifold 563 will normally cool the film to below its thermoplastic temperature, the passage of coolant through the chill roll as indicated by arrows 573, 574 in FIG. 17 will enable the apparatus to handle thicker films or to be operated at higher speeds.

To summarize, the first vacuum manifold 561, and the third vacuum manifold 563 located within the debossing/perforating cylinder 555 enable maintaining substantially constant upstream and downstream tension, respectively, in a running ribbon of film while the intermediate portion of the film adjacent the second vacuum manifold 562 within the debossing/perforating cylinder 555 is subjected to tension vitiating heat and vacuum to effect three-dimensional debossing and perforating of the film.

Referring again to FIG. 17, the constant tension film supply means 541 and the constant tension film forwarding and winding means 545 may, if desired, be substantially identical to and function substantially identically to the corresponding portions of the apparatus shown and described in commonly assigned U.S. Pat. No. 3,674,221 issued to Reimersma on July 4, 1972 and which is hereby incorporated herein by reference. The debossing and perforating means 543 comprises the rotatably mounted debossing/perforating cylinder 555, means (not shown) for rotating the cylinder 555 at a controlled peripheral velocity, the non-rotating triplex vacuum manifold assembly 556 inside the debossing-/perforating cylinder 555, means (not shown) for applying controlled levels of vacuum inside the three vacuum manifolds 561, 562, and 563 comprising the triplex manifold assembly 556, and hot air jet means 559.

The debossing/perforating cylinder 555 may be constructed by generally following the teachings of the aforementioned commonly assigned U.S. Patent of Malcolm B. Lucas and Robert H. Van Coney. However, the film-contacting surface of the tubular forming structure is provided with a fine scale pattern of surface aberrations corresponding to the pattern of surface aberrations desired in the visible surface of the resultant macroscopically expanded three-dimensional plastic film.

Figure 18:
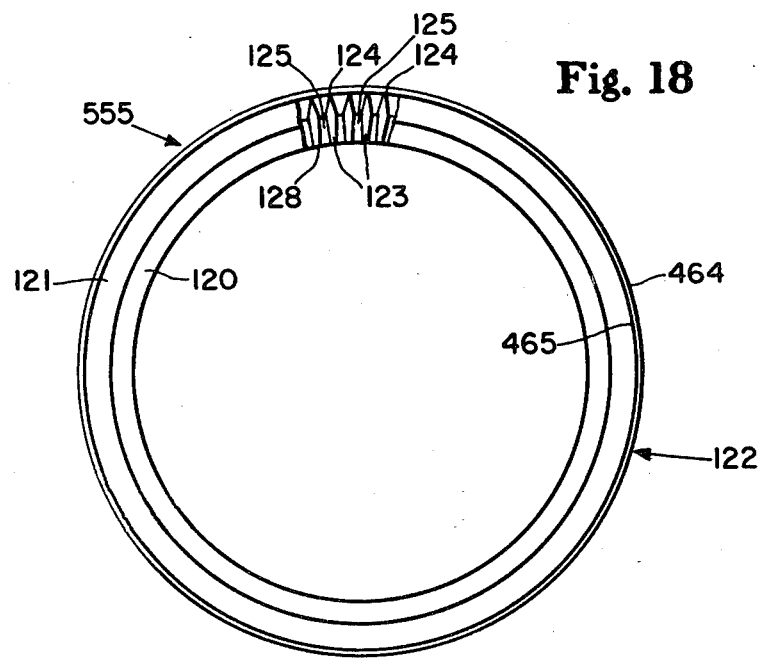
FIG. 18 is an enlarged end view of the debossing and perforating cylinder shown in FIG. 17.
Figure 19:
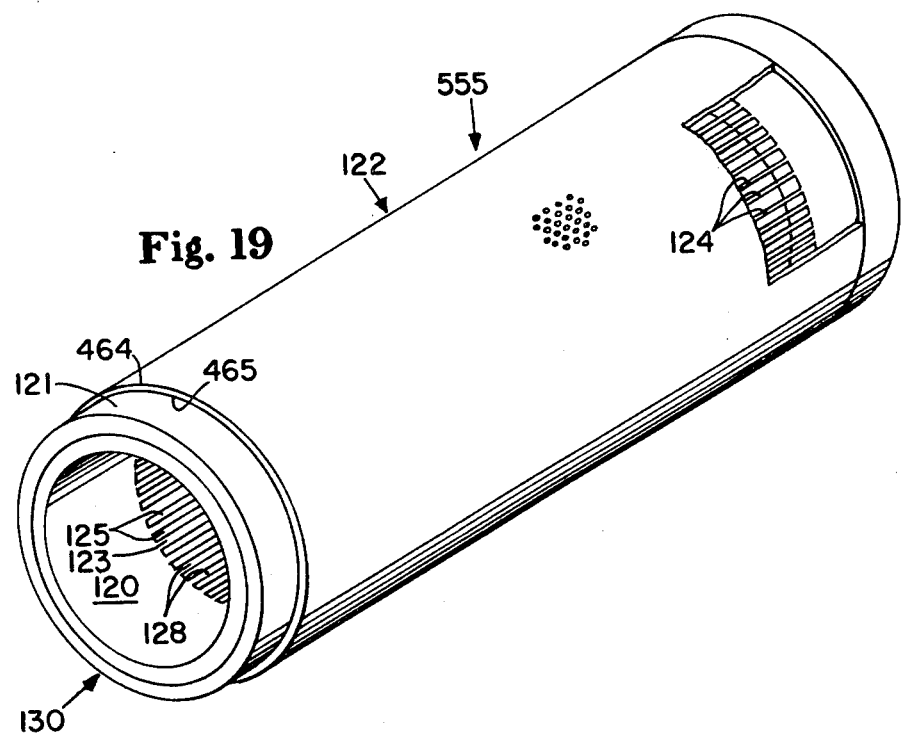
FIG. 19 is an enlarged perspective view of the debossing and perforating cylinder shown in FIGS. 17 and 18.

The debossing/perforating cylinder 555 shown in FIG. 17 is illustrated in greater detail in FIGS. 18 and 19. The cylinder 555 comprises a cage 120, a support ring 121 and a relatively thin walled film-contacting tubular member 122. The cage 120 comprises a multiplicity of circumferentially spaced, longitudinally extending bars 123 which are tapered to relatively small, radially outwardly facing lands 124. The spaced bars 123 have vacuum communicating passageways 125 provided therebetween. The bars 123 also have radially inwardly facing lands 128 which corporately provide a cylindrical vacuum sealing surface against which the vacuum seals associated with the triplex vacuum manifold 556 are biased. Thus, as the debossing/perforating cylinder 555 rotates, its vacuum sealing surface slides over the seals (not shown) of the non-rotating triplex vacuum manifold assembly 556.

The end 130, FIG. 19, of the debossing/perforating cylinder 555 disposed remotely from its driven end is open in order to provide easy insertion/removal of the triplex vacuum manifold assembly 556. Therefore, in order to rotatably support the open end 130 of cylinder 555, it is provided with a bearing-race support ring 121, as shown in FIGS. 18 and 19, which rides on bearings (not shown) which are appropriately secured to the apparatus frame (not shown).

Figure 20:
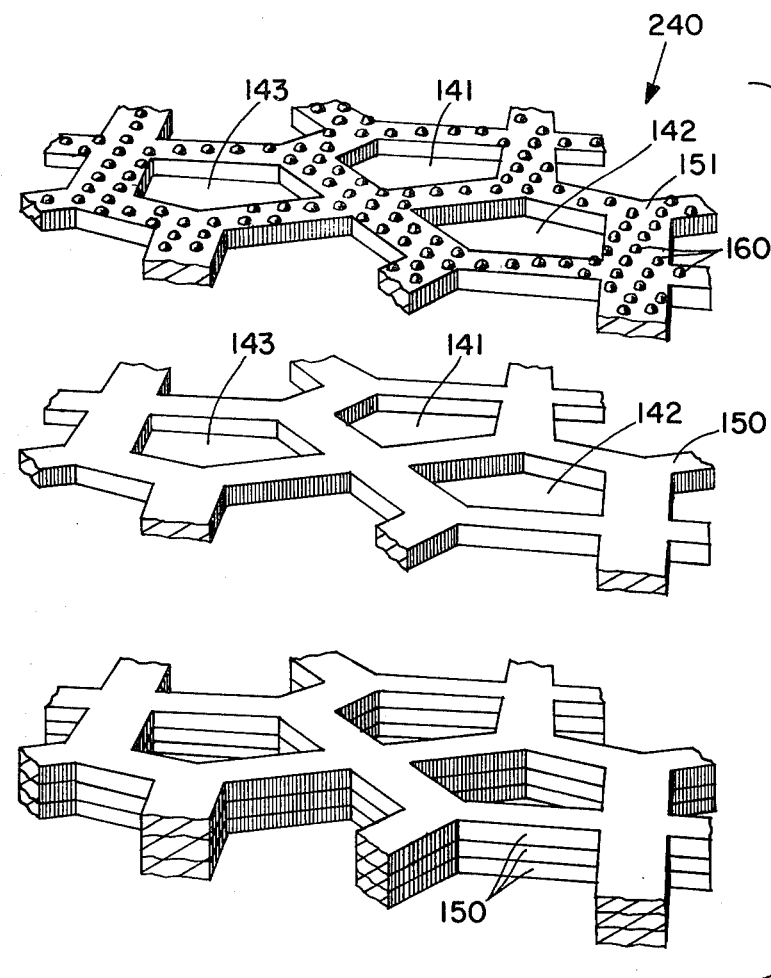
FIG. 20 is an enlarged, partially exploded segment of a preferred laminate film forming structure of the present invention (shown prior to rolling and seaming), said structure being particularly suitable for use in conjunction with one-sided forming processes of the type generally disclosed herein.

Tubular member 122 is fluid pervious and may comprise a relatively thin laminate structure such as 240, a partially exploded, enlarged planar segment of which is shown in FIG. 20, in contacting relation with the small lands 124 of the longitudinally extending support bars 123 of cage 120. The tubular member 122 is configured to deboss and perforate an extremely fine three-dimensional, apertured pattern into a relatively thin thermoplastic film such as low density polyethylene film, as will be described in greater detail hereinafter.

Only the outermost surface 464 of the tubular forming member 122 contacts the plastic webs brought in contact therewith. The innermost surface 465 of the tubular member contacts the lands 124 of support members 123 during the debossing/perforating operation.

The tubular member 122 shown in FIGS. 18 and 19 may be constructed generally in accordance with the teachings of the aforementioned commonly assigned, co-pending U.S. patent application of Clifford Radel and Hugh A. Thompson entitled RESILIENT PLASTIC WEB EXHIBITING FIBER-LIKE PROPERTIES AND METHOD AND APPARATUS FOR ITS MANUFACTURE, Ser. No. 206,410, filed Nov. 13, 1980, now U.S. Pat. No. 4,342,314 and incorporated herein by reference. The tubular member 122 may be constructed utilizing a stack of copper plated, photoetched metallic laminae exhibiting concentrically aligned patterns of apertures, said laminae being bonded to one another at contact points while subjected to heat and pressure. The resultant laminate structure is thereafter rolled into a tubular shape and its free edges are bonded to one another to form a continuous tubular forming structure generally in accordance with the teachings of the aforementioned patent application of Radel and Thompson.

FIG. 20 is a simplified embodiment of a particular laminate structure 240 which could, if desired, be utilized to provide a surface suitable for debossing and perforating an initially imperforate, substantially planar plastic web to produce a fluid-pervious macroscopically expanded three-dimensional plastic web exhibiting a fine scale pattern of pentagonally shaped capillary networks, each of said networks having a substantially constant cross-section along its length. The laminate structure 240 (shown prior to rolling and seaming) is comprised of a stack of identically apertured laminae. With the exception of the pattern of surface aberrations 160 present on uppermost lamina 151, laminae 150 and 151 are identical to one another. Each lamina has a pattern of irregular pentagonally shaped openings or apertures, e.g., apertures 141, 142, 143, therein. In the illustrated embodiment, laminae 150 and 151 are so stacked that the pentagonally shaped apertures in each successive lamina coincide with one another.

Laminae 150 are preferably formed from planar metallic sheets by photoetching techniques well known in the art, as described in the aforementioned patent application of Radel and Thompson. The uppermost surface of lamina 151, which coincides with the visible surface of plastic webs contacting tubular member 122, is also preferably photoetched by techniques well known in the art to provide a regularly spaced, microscopic pattern of protuberances, hereinafter generally referred to as surface aberrations 160. This is preferably accomplished by applying a resist coating which corresponds to the desired microscopic pattern of surface aberrations to the top side of a planar photoetched lamina 150, and thereafter initiating a second photoetching process. The second photoetching process produces a lamina 151 having a microscopic pattern of surface aberrations 160 on the interconnected fiber-like elements defining the pentagonally shaped apertures, e.g., apertures 141, 142, 143.

In order to construct a forming structure suitable for producing substantially non-glossy macroscopically expanded three-dimensional plastic webs of the present invention, it is necessary that the microscopic pattern of surface aberrations 160 be sufficiently small that said pattern, when imparted to an opaque plastic web, is non-discernible when the perpendicular distance between the viewer's eye and the plane of said web is about 12 inches or greater, that each of said surface aberrations 160 be free of any planar areas which are large enough that when imparted to an opaque plastic web, the resultant surface aberration in said web will be free of any planar areas which are large enough to inscribe a four mil (i.e., 0.004 inch) diameter circle, and that each of said surface aberrations 160 be so spaced relative to all adjacent surface aberrations 160 that, when imparted to an opaque plastic web, the maximum diameter of any circle which can be inscribed on any planar surface intermediate said surface aberration on said web and said adjacent surface aberrations on said web is less than about four mils (i.e., 0.004 inches). Because the thickness of said web will influence the size and spacing of the surface aberrations on the forming structure, it should be noted that forming structures utilized to produce substantially non-glossy macroscopically expanded three-dimensional webs of the present invention will not necessarily satisfy the criteria which must be met by the resultant webs. Furthermore, even if the size and spacing criteria are met by the forming structure, said forming structures are typically comprised of metals or other non-plastic materials having vastly different reflectance characteristics than the opaque plastic webs processed thereon. Accordingly, visual discernibility of the pattern of surface aberrations or the visual perception of gloss on the forming structure does not necessarily mean that plastic webs processed thereon will also exhibit gloss.

As utilized herein, an "adjacent" surface aberration shall be defined as any surface aberration which can be included within a pair of unobstructed straight, radially extending lines originating at the geometric center of the aberration under consideration and making tangential contact with the aberration being tested for adjacency.

In those situations where a more cloth-like or fiber-like tactile impression in the resultant macroscopically expanded three-dimensional plastic web is also desired, it has been found that the protuberances comprising surface aberrations 160 on lamina 151 should preferably exhibit an amplitude, i.e., the perpendicular distance from the top of said surface aberration to the plane in which said aberration originates, that is sufficient to produce an average amplitude of at least about 0.2 mils (i.e., 0.0002 inches) in the resultant plastic web, and most preferably at least about 0.3 mils (i.e., 0.0003 inches). In general, the greater the amplitude of the surface aberrations in the resultant plastic web, the more fiber-like said web will feel. In this regard it should also be noted that while the amplitude of said surface aberrations may vary considerably over the entire expanse of the resultant web, to optimize the fiber-like tactile impression of the web it is preferable that the amplitude of any particular surface aberration should not vary from the average value of the amplitude for all adjacent surface aberrations by more than about ±20 percent, and most preferably not more than about ±10 percent.

When the aforementioned criteria are met by the forming structure, the visible surface of webs which are macroscopically expanded so as to assume the three-dimensional pattern of said forming structure will appear non-glossy when the perpendicular distance between the viewer's eye and the plane of the web is about 12 inches or greater. If desired, the pattern of surface aberrations 160 on lamina 151 can be designed so that both the lamina-contacting and the non-lamina-contacting surfaces of the web coinciding with uppermost lamina 151 will appear non-glossy. This is due to the fact that substantially all of the light incident upon the visible surface of the web will be diffused into a multiplicity of directions by said surface aberrations, yet the pattern causing said diffusion is non-discernible to the naked eye under normal use conditions.

Because the sidewalls of the capillary networks formed by the coinciding apertures, e.g., apertures 141, 142, 143, do not exhibit any surface aberrations, these surfaces would appear glossy if they formed a portion of the web's visible surface, as viewed from the non-lamina contacting side of the macroscopically expanded three-dimensional plastic web. However, since the sidewall surfaces are oriented substantially perpendicular to the web's visible surface in the disclosed embodiment, light emanating from the non-lamina contacting side of the web and incident upon the sidewalls will not, under most conditions, be specularly reflected at a viewer observing the non-lamina contacting surface of the web. Accordingly, the entire non-lamina contacting surface of the resultant web will exhibit a substantially non-glossy appearance.

Conversely, light emanating from the lamina-contacting side of the web and incident upon the sidewalls will be specularly reflected at a viewer observing the lamina contacting surface of the web. Accordingly, the viewer will generally perceive the lamina contacting surface of the web as being glossy, despite the fact that the portion of the web coinciding with lamina 151 might exhibit a non-glossy appearance.

From the foregoing, it is clear that in order to impart a non-glossy appearance to macroscopically expanded three-dimensional plastic webs of the present invention, it is necessary that substantially all portions of a web's visible surface, i.e., those portions of the web which are visible when viewed substantially perpendicularly to the plane of the web from the side of interest, must exhibit a pattern of surface aberrations which satisfy the criteria set forth earlier herein. Thus, for forming structures exhibiting straight sidewalls which are oriented substantially perpendicular to the plane of the web, only those surfaces visible from an overhead plan view of the forming structure (when said structure is in a planar condition) need be provided with said pattern of surface aberrations. However, when said forming structures exhibit sidewalls which are not oriented substantially perpendicular to the plane of the web, those portions of the sidewalls which correspond to the visible surface of the web are preferably provided with said pattern of surface aberrations. The importance of such sidewall preparation will, of course, increase as the degree of sidewall taper increases, since increased sidewall taper generally means a greater degree of sidewall visibility and hence a greater potential for specular reflection.

As will be appreciated by those skilled in the art, forming structures exhibiting tapered sidewalls, whether of integral or laminate construction, may have their entire visible surfaces subjected to a photoetching process to impart the desired pattern of surface aberrations thereto. Where laminar structures of the type generally illustrated in FIG. 20 employ tapered sidewalls, the uppermost surface of all exposed laminae may be provided with the desired pattern of surface aberrations prior to assembly to ensure that those portions of the structure corresponding to the web's visible surface exhibit the desired pattern. Alternatively or additionally, the edges of the apertures may be scalloped to impart the desired surface aberrations to the tapered sidewalls of the resultant macroscopically expanded three-dimensional plastic webs.

While the preferred one-sided process disclosed in FIG. 17 simultaneously imposes the pattern of surface aberrations and the macroscopic three-dimensional pattern of the forming structure on the web, it will be appreciated by those skilled in the art that these operations could be performed sequentially from the same side of the web. That is, the web could be caused to conform to a first forming structure exhibiting the desired pattern of surface aberrations, removed from said first forming structure and thereafter macroscopically expanded on a second three-dimensional forming structure. In the latter situation, said first formating structure could comprise a woven wire mesh screen exhibiting a knuckle pattern which satisfies the gloss minimization criteria herein set forth.

As was pointed out earlier herein, one-sided processes of the type generally illustrated in FIG. 17 will work most effectively on films having a substantially uniform planar thickness of about two mils (i.e., 0.002 inches) or less. The basic operational steps generally disclosed in the automated process of FIG. 17 are substantially the same as the non-automated steps utilized to produce the webs disclosed in FIGS. 1-4, 5-8 and 9-12 from a substantially planar ribbon of one mil (i.e., 0.001 inch) thick opaque polyethylene film. On films having a substantially uniform planar thickness greater than about two mils it becomes difficult to transmit fine scale patterns of surface aberrations, which typically comprise protuberances, completely through the film's thickness with sufficient detail to yield the desired improvements in gloss reduction and tactile impression. Accordingly a two-sided process of the type generally disclosed in FIG. 21 is usually preferred when dealing with relatively thick films. The basic operational steps generally described in the automated process of FIG. 21 are substantially the same as the non-automated steps utilized to produce the web disclosed in FIGS. 13-16 from a substantially planar ribbon of one mil thick opaque polyethylene film.

It must, of course, be recognized that in most instances the surface aberrations produced in webs formed by such a two-sided process comprise depressions rather than protuberances. Nonetheless the same basic criteria must be met by the resultant web to provide gloss minimization. Namely, the regularly spaced, microscopic pattern of surface aberrations must be sufficiently small that the pattern is not discernible to the naked eye when the perpendicular distance between the viewer's eye and the plane of the web is about 12 inches or greater, each of said surface aberrations must be free of any planar areas which are large enough to inscribe a four mil (i.e., 0.004 inch) diameter circle, and each of said surface aberrations must be so spaced relative to all adjacent surface aberrations that the maximum diameter of any circle which can be inscribed on any planar surface intermediate said surface aberration and said adjacent surface aberrations is less than about four mils (i.e., 0.004 inches).

In those situations where a more cloth-like or fiber-like tactile impression in the resultant macroscopically expanded three-dimensional plastic web is also desired, it has been found that the surface aberrations in said web should preferably exhibit an average amplitude, i.e., the perpendicular distance from the bottom of said depression to the plane in which said depression originates, of at least about 0.2 mils (i.e., 0.0002 inches), and most preferably at least about 0.3 mils (i.e., 0.0003 inches).

Experience has demonstrated that a more cloth-like or fiber-like tactile impression is perceived in macroscopically expanded three-dimensional plastic webs which meet the aforementioned amplitude criteria whether the surface aberrations comprise protuberances or depressions. This is believed to be due to the fact that in either case the surface of the web is divided into at least two distinct planes separated from one another by a distance of at least 0.2 mils (i.e., 0.0002 inches). In the case of protuberances, it is the tops of the aberrations which contact the observer's skin, while in the case of depressions it is the planar surface in which said aberrations originate which contacts the observer's skin. Because said division is carried out in a fine microscopic pattern, it is believed that only the reduced area of contact with the uppermost surface of the web and not existence of the pattern is tactilely perceived. This seems consistent with the observation that the more cloth-like or fiber-like impression described herein is most readily perceived when macroscopically expanded three-dimensional plastic webs of the present invention are superposed on a substantially deformable substrate such as airfelt, sponge, cellulosic fibers, or any other material having generally similar deformation characteristics. It is believed that the deformable nature of the substrate prevents an observer touching the surface of the web from exerting a force sufficient to significantly deform or otherwise alter the surface characteristics of the web, thereby preserving the reduced area of contact with the observer's skin.

The two-sided process schematically illustrated in FIG. 21 is identical to that pictorially illustrated in FIG. 17 with three basic exceptions: first, freely rotatable lead-on idler roll 565 has been eliminated, and a suction roll 665 which is driven in conjunction with debossing-/perforating cylinder 555 has been installed in its place; second, the web contacting surface of debossing/perforating cylinder 555 need not be provided with a fine scale pattern of surface aberrations 160; and third, a hot air jet means 659 generally similar to hot air jet means 559 has been installed adjacent the surface of suction roll 655. Suction roll 665 is provided with a porous web contacting surface which, in a particularly preferred embodiment, comprises a fine mesh wire screen.

A stationary suction chamber (not shown) located interiorly of suction roll 665 permits suction to be applied to the roll contacting surface of the imperforate substantially planar plastic web 550 substantially throughout the area of contact therebetween. The imperforate substantially planar plastic web 550 is preferably heated to its softening temperature by hot air jet means 659, so that the suction applied by roll 665 and the mechanical pressure which may, if desired, be applied in the nip between suction roll 665 and debossing-/perforating cylinder 555 have imparted the knuckle pattern exhibited by suction roll 665 to the suction roll contacting surface of the substantially planar web 550 by the time the web passes out of the nip.

By making certain that the pattern of surface aberrations thus imparted to the entire surface of the substantially planar plastic web 550 meets the criteria required for gloss elimination and improved tactile impression, as set forth earlier herein, the substantially planar web 550 may thereafter be processed, with minor exceptions, generally in accordance with the teachings of the aforementioned patent to Lucas et al. to provide a macroscopically expanded three-dimensional plastic web exhibiting a substantially non-glossy visible surface and a more cloth-like or fiber-like tactile impression.

The exceptions to the teachings of the Lucas et al. patent relate generally to a reduction in temperature of the plastic web 550 during the three-dimensional debossing and, if desired, aperturing operation. To avoid substantially washing out the pattern of surface aberrations imparted to the suction roll contacting surface of web 550 by suction cylinder 655, the temperature of the web is preferably not elevated substantially beyond its softening temperature during the subsequent debossing and perforating operations. Accordingly, somewhat higher suction levels may be required in the debossing and perforating portion of cylinder 555 to achieve the desired macroscopic expansion of the web than is the case for a higher temperature one-sided process of the type generally illustrated in FIG. 17.

While any porous three-dimensional surface which satisfies the requirements for gloss elimination described earlier herein may be used as a web contacting surface on suction roll 665, the knuckle patterns of fine mesh wire screens have been found particularly suitable. In particular, for filament diameters between about one and about two mils (i.e., between about 0.001 and about 0.002 inches), screens having mesh counts ranging from about 160 filaments per lineal inch by 160 filaments per lineal inch to about 400 filaments per lineal inch by 400 filaments per lineal inch have been found operable, with screens having about 250 filaments per lineal inch by 250 filaments per lineal inch being optimal. The larger filament diameters are generally operable with mesh counts at the lower end of the range, while the smaller filament diameters are generally operable with mesh counts at the upper end of the range. The weave pattern of the screen may be varied as desired, so long as the resultant pattern of surface aberrations produced in the web satisfies the gloss reduction and tactile impression criteria described earlier herein.

As will be appreciated by those skilled in the art, when the web contacting surface of suction roll 665 is a wire screen, the screen may be permanently secured to the periphery of the roll or fed in the form of a continuous belt across the web contacting surface of suction roll 665. In the latter embodiment, the screen may, if desired, serve as a carrier belt and remain in contact with debossing/perforating cylinder 555 through at least a portion of the web's trajectory. Both alternatives are schematically illustrated in FIGS. 3 and 4, respectively, of U.S. Pat. No. 2,776,451 issued to Chavannes on Jan. 8, 1957, said patent being hereby incorporated herein by reference.

It will also be appreciated by those skilled in the art that the order in which the steps of the two-sided process generally disclosed in FIG. 21 are carried out could be reversed, i.e., the web could be macroscopically expanded to its three-dimensional profile and thereafter brought in contact with a forming structure exhibiting the desired pattern of surface aberrations while said web is still being supported on said three-dimensional forming structure. The latter arrangement may find particular utility where the macroscopically expanded three-dimensional webs exhibit capillary networks having sidewalls oriented substantially perpendicular to the plane of said web.

As will be further appreciated by those skilled in the art, while the one-sided process generally described in connection with FIG. 17 and the two-sided process generally described in conjunction with FIG. 21 have dealt with converting substantially planar plastic webs into macroscopically expanded three-dimensional plastic webs, the present invention may be practiced with equal facility where resinous melts are involved.

Figure 22:
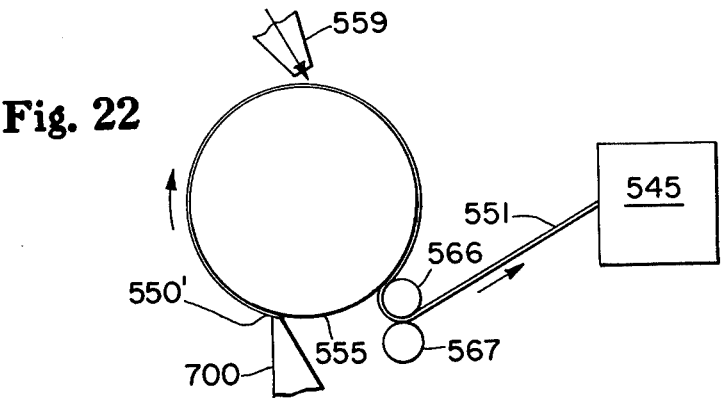
FIG. 22 is a simplified schematic illustration of a preferred one-sided film forming process of the present invention wherein a resinous melt is extruded directly onto the surface of a debossing and perforating cylinder having a microscopic pattern of surface aberrations thereon.

A one-sided process of this type is schematically disclosed in FIG. 22, wherein a resinous melt 550' is extruded by means of extruder 700 directly onto the surface of a debossing/perforating cylinder 555 exhibiting a microscopic pattern of surface aberrations about its periphery. Depending upon the proximity of the extruder 700 to the point of debossing and perforating and the temperature of the resinous melt 550' at said point, hot air jet means 559 may prove unnecessary.

Figure 23:
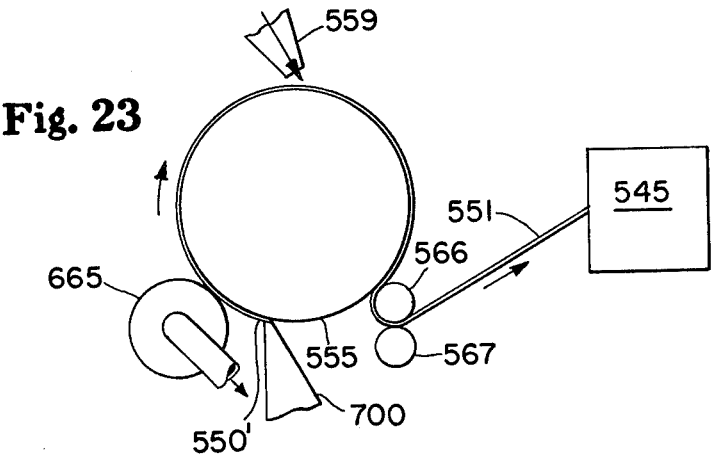
FIG. 23 is a simplified schematic illustration of a preferred two-sided film forming process of the present invention wherein a resinous melt is extruded directly onto the surface of a debossing and perforating cylinder and the opposite surface of said melt is thereafter contacted by a suction roll to impart a microscopic pattern of surface aberrations thereto.

An exemplary two-sided process employing a resinous melt is schematically disclosed in FIG. 23. The process of FIG. 23 is generally similar to the one-sided process of FIG. 22, but suction roll 665 has been added to impart the desired pattern of surface aberrations to the suction roll contacting surface of the resultant plastic web. Accordingly it is not necessary to provide a microscopic pattern of surface aberrations about the periphery of debossing/perforating cylinder 555. It will, of course, be recognized by those skilled in the art that the extruder 700 could with equal facility be positioned to apply resinous melt 550' directly onto the surface of suction roll 665 for subsequent transfer to the surface of debossing/perforating cylinder 555.

While particular embodiments of the present invention have been illustrated and described, it will be obvious to those skilled in the art that various changes and modifications can be made without departing from the spirit and scope of the invention. For example, the manufacturing processes generally disclosed in FIGS. 17 and 21–23 might be carried out by means of mechanical compression either solely or in combination with fluid pressure differentials, the one-sided and two-sided processes might be carried out in conjunction with one another to produce superposed patterns of surface aberrations, protuberances and depressions might be combined with one another in a single regularly spaced, microscopic pattern of surface aberrations, etc. It is intended to cover in the appended claims all such modifications that are within the scope of this invention.

What is claimed is:

1. A macroscopically expanded three-dimensional plastic web having at least one visible surface which appears substantially non-glossy when exposed to light, substantially all of said visible surface exhibiting a regularly spaced, microscopic pattern of discrete surface aberrations, each of said surface aberrations having its amplitude oriented perpendicular to the surface in which said surface aberration originates, each of said surface aberrations having a maximum dimension of less than about 6 mils, as measured in a plane oriented substantially perpendicular to its amplitude, whereby said surface aberrations are not discernible to the normal naked eye when the perpendicular distance between the viewer's eye and the plane of said web is at lest about 12 inches, each of said surface aberrations also being free of planar areas which are large enough to inscribe a 4 mil diameter circle and so spaced relative to all adjacent surface aberrations that the maximum diameter of any circle which can be inscribed on any planar surface intermediate said surface aberration and said adjacent surface aberrations on any portion of said visible surface is less than about 4 mils, whereby any light incident upon any portion of said visible surface is diffusely reflected into a multiplicity of directions by said surface aberrations so that said visible surface appears substantially non-glossy.

2. The web of claim 1, wherein at least a portion of said surface aberrations comprise protuberances projecting generally outwardly from the surface of said web.

3. The web of claim 1, wherein at least a portion of said surface aberrations comprise depressions projecting generally inwardly from the surface of said web.

4. The web of claim 3, wherein said surface aberrations correspond to the knuckles of a woven mesh support structure which directly contacts the visible surface of said plastic web during production thereof.

5. The web of claim 4, wherein said woven mesh support structure which directly contacts the visible surface of said web is comprised of filaments having a diameter between about one and about two mils and a mesh count between about 160 filaments per lineal inch by 160 filaments per lineal inch and about 400 filaments per lineal inch by 400 filaments per lineal inch.

6. The web of claim 2 or claim 3, wherein said surface aberrations have an average amplitude of at least about 0.2 mils.

7. The web of claim 2 or claim 3, wherein said surface aberrations have an average amplitude of at least about 0.3 mils.

8. The web of claim 6, wherein the amplitude of each of said surface aberrations, as measured perpendicular to the surface in which said surface aberration originates, is within the range of about ±20 percent of the average value of the amplitude for all adjacent surface aberrations.

9. The web of claim 6, wherein the amplitude of each of said surface aberrations, as measured perpendicular to the surface in which said surface aberration originates, is within the range of about ±10 percent of the average value of the amplitude for all adjacent surface aberrations.

* * * * *

UNITED STATES PATENT AND TRADEMARK OFFICE
CERTIFICATE OF CORRECTION

PATENT NO. : 4,463,045

DATED : July 31, 1984

INVENTOR(S) : NICHOLAS A. AHR, PAUL R. LOUIS, WILLIAM I. MULLANE, WILLIAM R. OUELLETTE

It is certified that error appears in the above-identified patent and that said Letters Patent is hereby corrected as shown below:

Abstract, page 2, column 1, line 8, "inveniton" should read -- invention --.

Column 2, line 65, "of" should read -- thereof. --.

Column 4, line 1, "Sorenson" should read -- Sorensen --.

Column 4, line 22, "Sorenson" should read -- Sorensen --.

Column 4, line 45, "Sorenson" should read -- Sorensen --.

Column 6, line 9, "Sorenson" should read -- Sorensen --.

Column 6, line 15, "generaly" should read -- generally --.

Column 8, line 55, "imge-" should read -- image- --.

Column 8, line 56, "reference" should read -- reflectance --.

Column 9, line 19, "Sorenson" should read -- Sorensen --.

Column 9, line 34, "Sorenson" should read -- Sorensen --.

Column 10, line 39, "Sorenson" should read -- Sorensen --.

UNITED STATES PATENT AND TRADEMARK OFFICE
CERTIFICATE OF CORRECTION

PATENT NO. : 4,463,045

DATED : July 31, 1984

INVENTOR(S) : NICHOLAS A. AHR, PAUL R. LOUIS, WILLIAM I. MULLANE, WILLIAM R. OUELLETTE

It is certified that error appears in the above-identified patent and that said Letters Patent is hereby corrected as shown below:

Column 21, line 37, "formating" should read -- forming --.

Column 25, line 14, Claim 1, "lest" should read -- least --.

Signed and Sealed this

Twenty-ninth Day of October 1985

[SEAL]

Attest:

DONALD J. QUIGG

Attesting Officer

Commissioner of Patents and Trademarks—Designate